US011065430B2

(12) United States Patent
Zergiebel et al.

(10) Patent No.: US 11,065,430 B2
(45) Date of Patent: Jul. 20, 2021

(54) COUPLING DEVICES FOR TUBE SETS USED WITH SURGICAL GAS DELIVERY SYSTEMS

(71) Applicant: Surgiquest, Inc., Milford, CT (US)

(72) Inventors: Earl M. Zergiebel, Guilford, CT (US); Michael J. Augelli, Prospect, CT (US); Kenneth Blier, Cheshire, CT (US)

(73) Assignee: Surgiquest, Inc., Milford, CT (US)

( * ) Notice: Subject to any disclaimer, the term of this patent is extended or adjusted under 35 U.S.C. 154(b) by 487 days.

(21) Appl. No.: 15/685,607

(22) Filed: Aug. 24, 2017

(65) Prior Publication Data

US 2017/0361084 A1  Dec. 21, 2017

Related U.S. Application Data

(63) Continuation of application No. 15/241,960, filed on Aug. 19, 2016.
(Continued)

(51) Int. Cl.
*A61M 39/10* (2006.01)
*A61B 17/34* (2006.01)
(Continued)

(52) U.S. Cl.
CPC ..... *A61M 39/1011* (2013.01); *A61B 17/3474* (2013.01); *A61M 13/003* (2013.01);
(Continued)

(58) Field of Classification Search
CPC ...................................... A61M 39/105; A61M 2039/1077–2039/1088; A61M 39/12;
(Continued)

(56) References Cited

U.S. PATENT DOCUMENTS

| 5,312,363 A | 5/1994 | Ryan et al. |
| 5,538,509 A | 7/1996 | Dunlap et al. |

(Continued)

FOREIGN PATENT DOCUMENTS

WO  WO-2007/028232  3/2007

OTHER PUBLICATIONS

International Search Report and Written Opinion for PCT Application No. PCT/US2016/047741, dated Nov. 3, 2016.
(Continued)

*Primary Examiner* — Bradley J Osinski
(74) *Attorney, Agent, or Firm* — Locke Lord LLP; Scott D. Wofsy

(57) ABSTRACT

The subject invention is directed to a new and useful coupling system for connecting a tube set to a trocar. More particularly, the system includes a trocar connector having no more than two coaxial flow passages formed therein including an inner flow passage and an outer flow passage. The inner flow passage is defined by an inner annular wall and the outer flow passage is defined between the inner annular wall and an outer annular wall. A dual lumen tube set is included with a first tube having a first diameter and a second tube having a second diameter that is greater than the diameter of the first tube. The system further includes a coupling including a generally cylindrical body having a first end portion configured to mate with the two coaxial flow passages of the trocar connector and a second end portion configured for attachment to the two tubes of the dual lumen tube set.

14 Claims, 23 Drawing Sheets

Related U.S. Application Data

(60) Provisional application No. 62/208,169, filed on Aug. 21, 2015.

(51) Int. Cl.
*A61M 13/00* (2006.01)
*A61M 16/08* (2006.01)
*A61M 25/00* (2006.01)
*A61B 17/00* (2006.01)

(52) U.S. Cl.
CPC .... *A61M 16/0816* (2013.01); *A61M 25/0014* (2013.01); *A61M 39/105* (2013.01); *A61B 2017/00477* (2013.01); *A61M 2039/1027* (2013.01)

(58) Field of Classification Search
CPC .......... A61M 39/1011; A61M 25/0014; A61M 16/0816; A61M 2039/1027; A61M 2017/00477
See application file for complete search history.

(56) References Cited

U.S. PATENT DOCUMENTS

| | | | |
|---|---|---|---|
| 5,702,374 A * | 12/1997 | Johnson | A61M 39/10 128/912 |
| 5,899,899 A * | 5/1999 | Arless | A61B 18/02 606/20 |
| 6,319,266 B1 | 11/2001 | Stellon et al. | |
| 2003/0028182 A1* | 2/2003 | Abboud | A61B 18/02 606/21 |
| 2009/0137943 A1* | 5/2009 | Stearns | A61M 13/006 604/26 |
| 2014/0171855 A1* | 6/2014 | Mastri | A61M 39/1011 604/26 |

OTHER PUBLICATIONS

Australian Examination Report dated Mar. 17, 2020, issued during the prosecution of Australian Patent Application No. AU 2016310484.

* cited by examiner

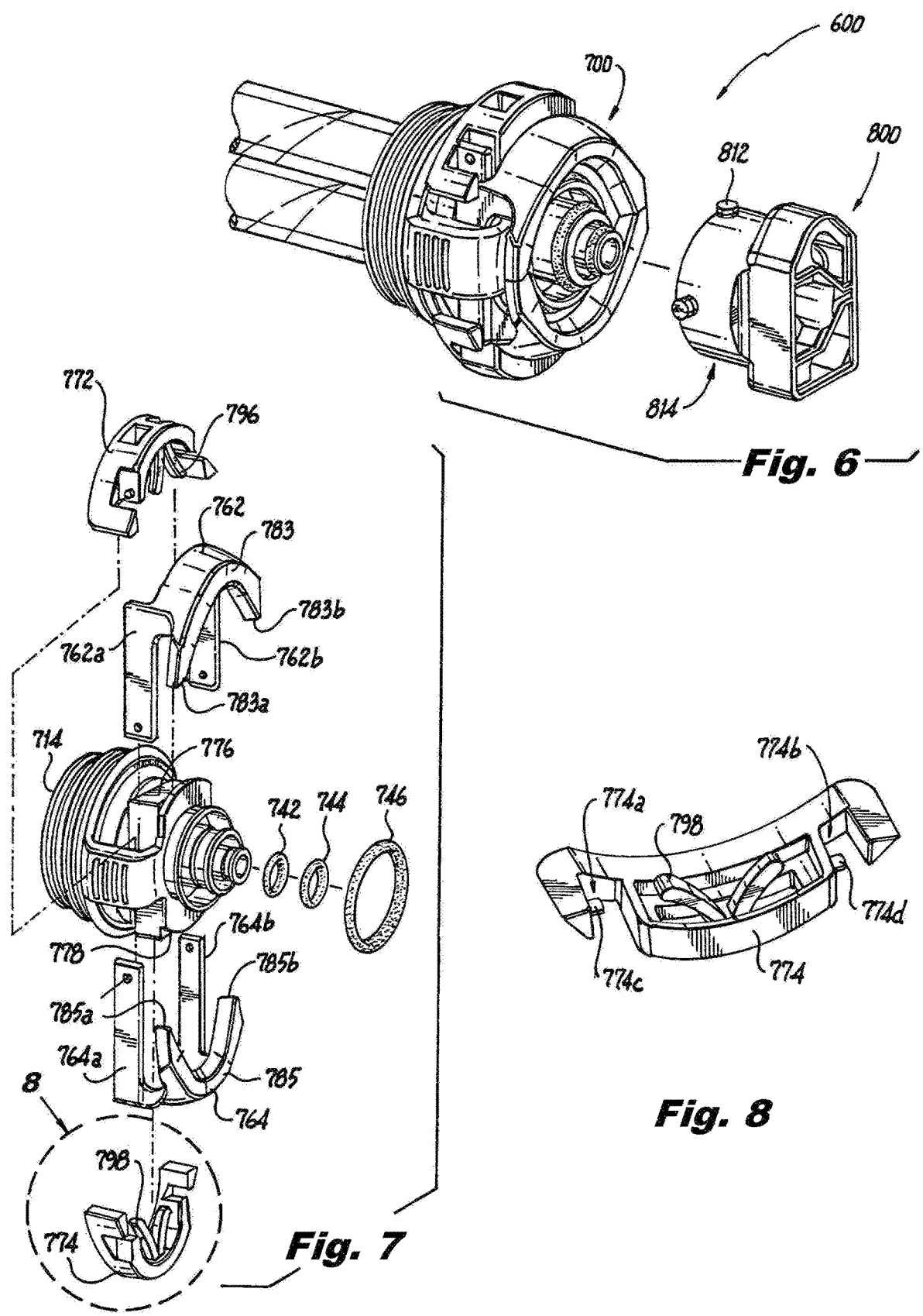

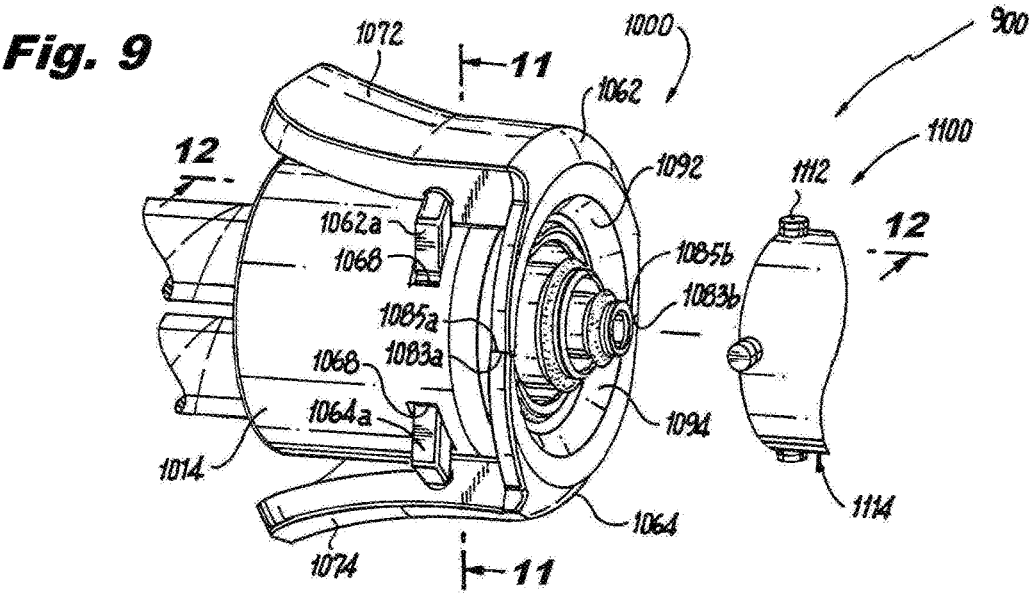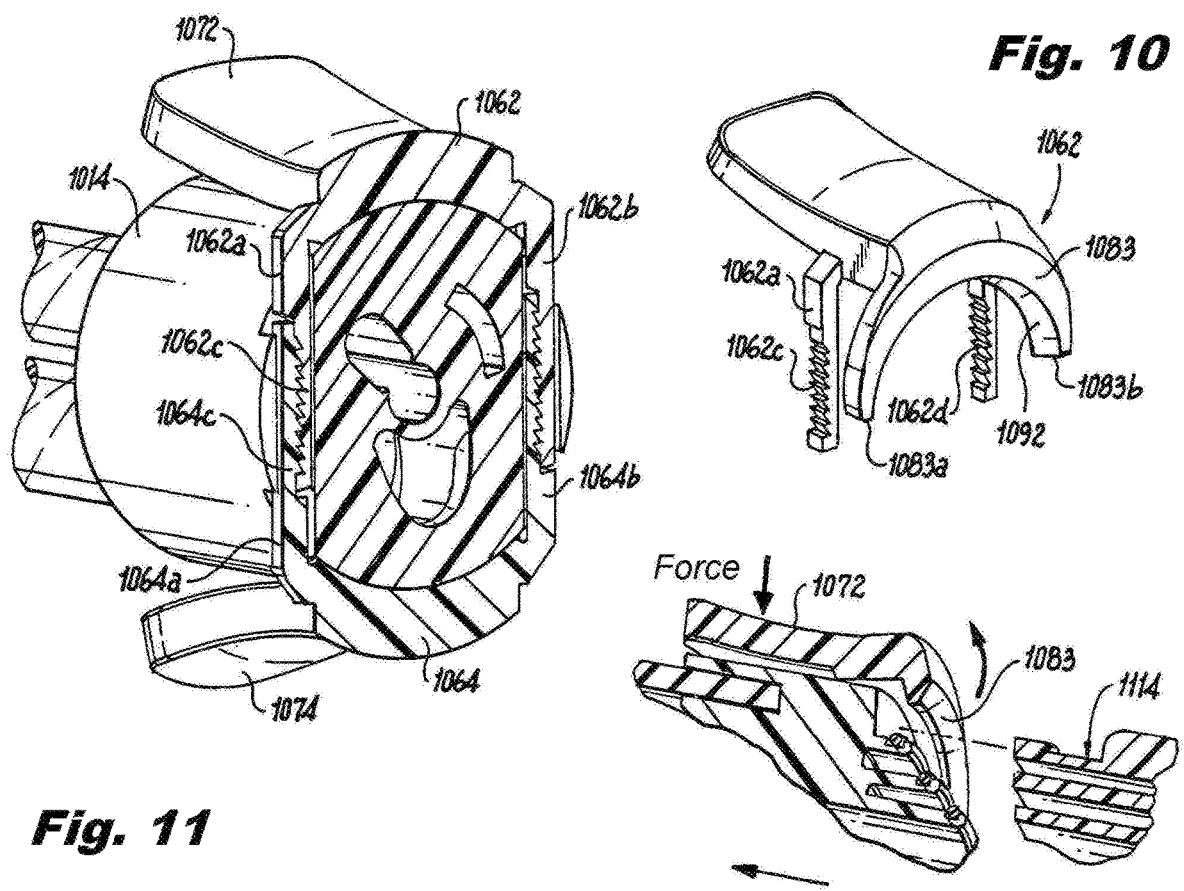

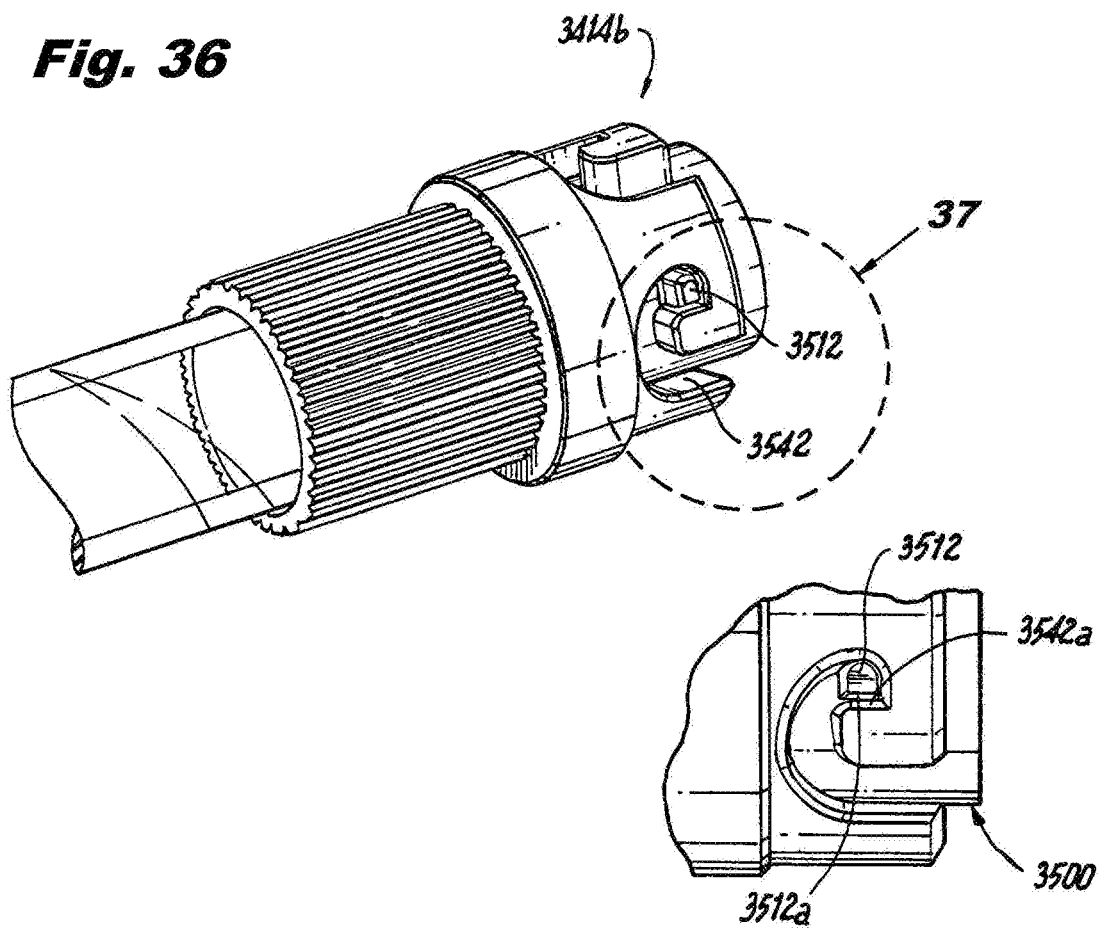
Fig. 36
Fig. 37
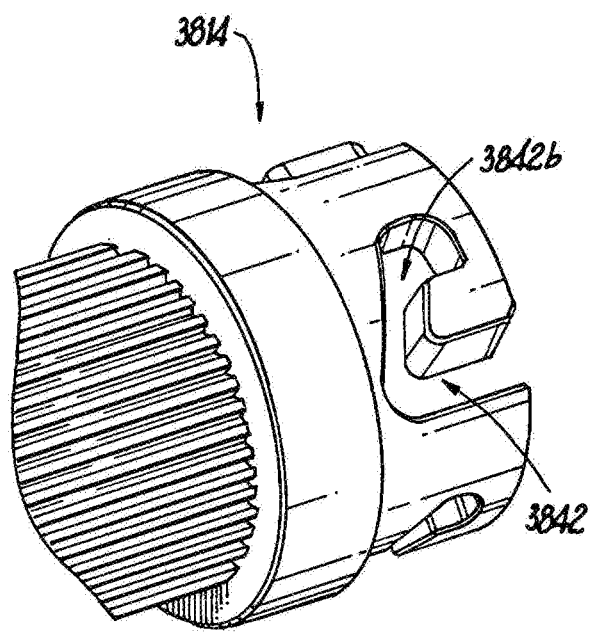
Fig. 38

COUPLING DEVICES FOR TUBE SETS USED WITH SURGICAL GAS DELIVERY SYSTEMS

CROSS-REFERENCE TO RELATED APPLICATION

The subject invention is a continuation of U.S. application Ser. No. 15/241,960 filed Aug. 19, 2016, which claims the benefit of and priority to U.S. Provisional Application Ser. No. 62/208,169 filed Aug. 21, 2015, which are herein incorporated by reference in their entirety.

BACKGROUND OF THE INVENTION

1. Field of the Invention

The subject invention is directed to a mechanical coupling, and more particularly, to a coupling device for connecting a multi-lumen tube set to a surgical access device used during minimally invasive surgical procedures for delivering surgical gas.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a surgical access device (sometimes referred to as a "cannula" or "trocar") equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum. During typical laparoscopic procedures, a surgeon makes three to four small incisions, usually no larger than about twelve millimeters each, which are typically made with the surgical access devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duck-bill-type valve made of a relatively pliable material, to seal around an outer surface of surgical instruments passing through the trocar.

Further, in laparoscopic surgery, electrocautery and other techniques (e.g. harmonic scalpels) create smoke and other debris in the surgical cavity, reducing visibility by fogging the view from, and coating surfaces of endoscopes and the like. A variety of surgical insufflation systems and smoke evacuation systems are known in the art.

SurgiQuest of Milford, Conn. has developed surgical access devices or trocars that permit access to an insufflated surgical cavity without conventional mechanical seals, and has developed related systems for providing sufficient pressure and flow rates to such access devices, as described in whole or in part in U.S. Pat. No. 7,854,724, the disclosure of which is herein incorporated by reference in its entirety.

SurgiQuest has also developed multimodal systems, and related devices and methods, capable of performing multiple surgical gas delivery functions, including insufflation to standard or specialized surgical access devices or other instruments, such as veress needles and the like, smoke evacuation through standard or specialized surgical access devices, and specialized functions, such as recirculation and filtration of insufflation fluids. Examples of such multimodal systems and related devices are disclosed in U.S. Patent Application Publication 2012/0150101, which is herein incorporated by reference in its entirety.

Multimodal systems typically require the use of a disposable filter cartridge having multiple flow passages, as disclosed in U.S. Pat. No. 7,976,598 and U.S. Patent Application Publication No. 2013/0231606, which are herein incorporated by reference in their entireties. These disposable filter cartridges are installed in an insufflator and are connected to a multi-lumen tube set which communicates with a surgical access device or trocar, such as, for example, the devices disclosed in U.S. Patent Application Publication 2012/0245511, which is incorporated herein by reference in its entirety.

The mechanical connection between the tube set and the surgical access device or trocar is typically a threaded connection and often requires precise alignment of a plurality of flow paths. Achieving this connection can take an inordinate amount of time and can require some level of dexterity. A unique coupling system for detachably connecting a multi-lumen tube set to a surgical access device that overcomes these deficiencies is described in U.S. Patent Application Publication No. 2014/0171855, the disclosure of which is herein incorporated by reference in its entirety. This connection, which is in the form of a unique triple luer type fitting, is relatively difficult to manufacture in a cost effective manner. It would be beneficial therefore, to provide a coupling device for aligning a plurality of flow channels that is easier to manufacture in a more cost effective manner.

SUMMARY OF THE INVENTION

The subject invention is directed to a new and useful coupling system for connecting a tube set to a trocar. More particularly, the system includes a trocar connector having no more than two coaxial flow passages formed therein including an inner flow passage and an outer flow passage. The inner flow passage is defined by an inner annular wall and the outer flow passage is defined between the inner annular wall and an outer annular wall. A dual lumen tube set is included with a first tube having a first diameter and a second tube having a second diameter that is greater than the diameter of the first tube. The system further includes a coupling including a generally cylindrical body having a first end portion configured to mate with the two coaxial flow passages of the trocar connector and a second end portion configured for attachment to the two tubes of the dual lumen tube set.

Preferably, the first end portion of the body has an inner flow passage defined by an inner annular wall for establishing fluid communication with the inner flow passage of the trocar connector and an outer flow passage defined between the inner annular wall and an outer annular wall for establishing fluid communication with the outer flow passage of the trocar connector. The second end portion of the body includes first and second parallel interior recesses. The first interior recess is dimensioned and configured to receive a distal end portion of the first tube of the dual lumen tube set. The second interior recess is dimensioned and configured to receive a distal end portion of the second tube of the dual lumen tube set.

In addition, the inner annular wall of the coupling is dimensioned and configured to fit within the inner annular wall of the trocar connector and the outer annular wall of the coupling is dimensioned and configured to fit within the outer annular wall of the trocar connector. The coupling further includes an outer shroud that surrounds the outer annular wall of the coupling. An inner surface of the shroud is threaded to rotatably interact with a plurality of posts that project radially outwardly from the outer annular wall of the trocar connector.

The first interior recess is configured for receiving the first tube of the dual lumen tube set to communicate with the outer flow passage of the coupling. The second interior recess is configured for receiving the second tube of the dual lumen tube set to communicate with the inner flow passage of the coupling. The first and second interior recesses are both off set from a central axis of the body of the coupling.

The subject invention is also directed to a coupling system for connecting a dual lumen tube set to a trocar having no more than two coaxial flow passages formed therein. A dual lumen tube set includes a first tube having a first diameter and a second tube having a second diameter that is greater than the diameter of the first tube. The system also includes a coupling with a generally cylindrical body having a first end portion configured to mate with the two coaxial flow passages of the trocar connector and a second end portion configured for attachment to the two tubes of the dual lumen tube set.

Preferably, the second end portion of the body includes first and second parallel interior recesses off set from a central axis of the body. The first interior recess is dimensioned and configured to receive a distal end portion of the first tube of the dual lumen tube set and the second interior recess is dimensioned and configured to receive a distal end portion of the second tube of the dual lumen tube set.

The trocar connector has an inner flow passage defined by an inner annular wall and an outer flow passage defined between the inner annular wall and an outer annular wall.

The first end portion of the coupling body has an inner flow passage defined by an inner annular wall for establishing fluid communication with the inner flow passage of the trocar connector. The first end portion also includes an outer flow passage defined between the inner annular wall and an outer annular wall for establishing fluid communication with the outer flow passage of the trocar connector. The inner annular wall of the coupling is dimensioned and configured to fit within the inner annular wall of the trocar connector and the outer annular wall of the coupling is dimensioned and configured to fit within the outer annular wall of the trocar connector.

The first interior recess is configured for receiving the first tube of the dual lumen tube set to communicate with the outer flow passage of the coupling. The second interior recess is configured for receiving the second tube of the dual lumen tube set to communicate with the inner flow passage of the coupling.

In one embodiment, the coupling includes an outer shroud that surrounds the outer annular wall of the coupling and an inner surface of the shroud is threaded to rotatably interact with a plurality of posts that project radially outwardly from the outer annular wall of the trocar connector.

The subject invention is also directed to a coupling for connecting a dual lumen tube set to a trocar including a generally cylindrical body having a first end portion configured to mate with a trocar connector having no more than two co-axial flow passages and a second end portion configured for attachment to a dual lumen tube set.

Preferably, the first end portion of the body has an inner flow passage defined by an inner annular wall for establishing fluid communication with an inner flow passage of the trocar connector. The first end portion also has an outer flow passage defined between the inner annular wall and an outer annular wall for establishing fluid communication with an outer flow passage of the trocar connector.

In addition, the second end portion of the body includes first and second parallel interior recesses. The first interior recess is dimensioned and configured to receive a distal end portion of a first tube of the dual lumen tube set. The second interior recess is dimensioned and configured to receive a distal end portion of the second tube of the dual lumen tube set. The first interior recess has a first inner diameter and the second interior recess has a second inner diameter that is greater than the diameter of the first interior recess.

In one embodiment, an outer shroud surrounds the outer annular wall of the coupling and an inner surface of the shroud is threaded to rotatably interact with the trocar connector.

These and other features of the coupling system of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the coupling assembly of the subject invention without undue experimentation, preferred embodiments thereof will be described in detail herein below with reference to certain figures, wherein:

FIG. 6 is a perspective view of an alternate embodiment of a coupling assembly for a tri-lumen tube set, showing a coupler and mating device;

FIG. 7 is an exploded perspective view of the coupler of FIG. 6, showing symmetrical flexible tabs of the latch assemblies;

FIG. 8 is a detailed view of the flexible tabs of the coupler of FIGS. 6 and 7;

FIG. 9 is a perspective view of an alternate embodiment of a coupling assembly for a tri-lumen tube set, showing a coupler and mating device;

FIG. 10 is a perspective view of a latch assembly of the coupler of FIG. 9;

FIG. 11 is a cross-sectional view taken along line 11-11 of FIG. 9, showing ratchet teeth of each latch assembly;

FIG. 12 is a cross-sectional view taken along line 12-12 of FIG. 9, showing removal of coupler from mating device;

FIG. 36 is a perspective view of the coupler of FIG. 34 with post of mating device fully locked within the respective cam slot;

FIG. 37 is a detailed view of the mating device post within the cam slot of FIG. 36;

FIG. 38 is an alternate embodiment of the cam slot;

DETAILED DESCRIPTION OF PREFERRED EMBODIMENTS

Figure 1:
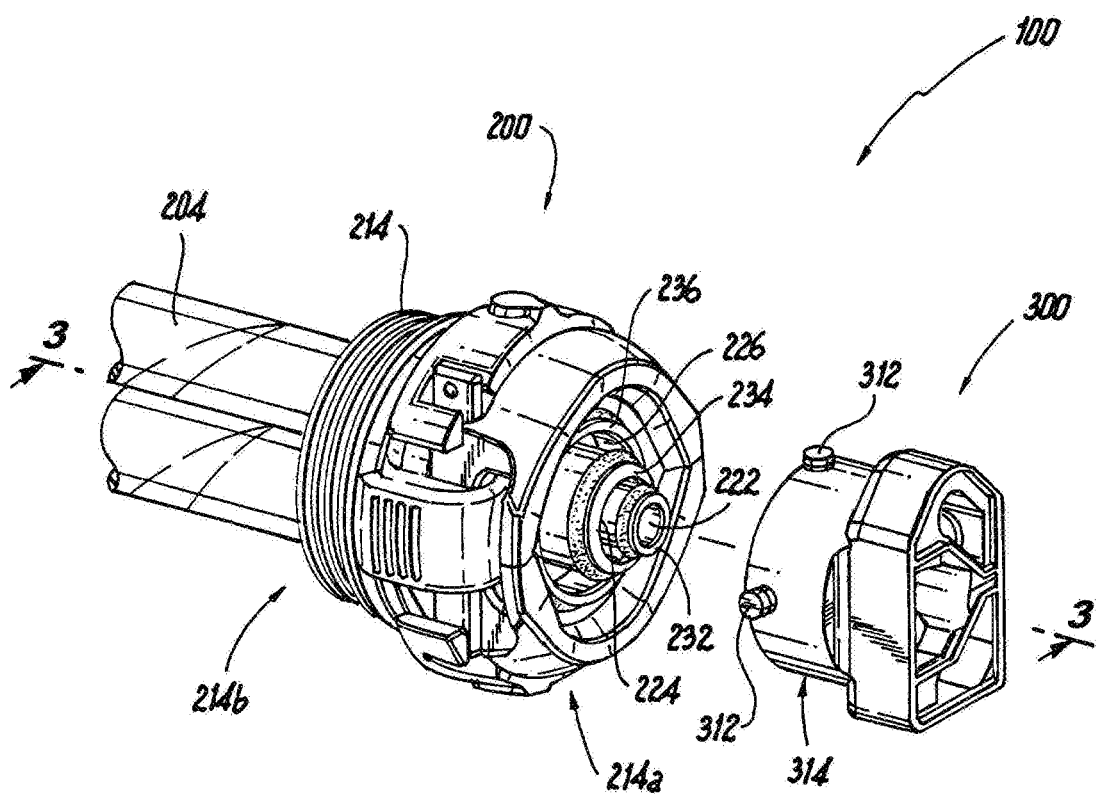
FIG. 1 is a perspective view of a coupling assembly for a tri-lumen tube set in accordance with the subject invention, showing a coupler and a mating device configured to connect a tube set to a trocar.

Referring now to the drawings wherein like reference numerals identify similar structural features and/or elements of the subject matter disclosed herein, there is illustrated in FIG. 1 a system for releasably coupling a tube set to a surgical device constructed in accordance with a preferred embodiment of the subject invention and designated generally by reference numeral 100.

In the description that follows, FIGS. 1-20 include couplers and mating devices designed to upgrade the current tri-lumen system, FIGS. 21-26 illustrate dual lumen connectors, and FIGS. 27-65 include features for single lumen couplers.

I. Tri-Lumen Coupling Assemblies

Referring to FIG. 1, coupling assembly 100 includes a coupler 200 adapted and configured to selectively connect the coupler 200 to a connector (mating device) 300 for incorporation with a surgical device (e.g., a trocar). The features of the coupler 200 and mating device 300 described herein are designed to upgrade the current tri-lumen coupler, as disclosed for example in U.S. Patent Publication 2014/0171855, which is incorporated herein by reference in its entirety, and to allow for better manufacturing while still being backwards compatible with current mating devices. The features of the surgical device that is envisioned for use with the coupler 200 is explained in more detail in U.S. Pat. No. 7,854,724, which is incorporated herein by reference in its entirety, and shall not be discussed in detail herein.

With reference to FIGS. 1-4, the coupler 200 includes an elongated generally cylindrical body 214 having opposed distal 214a and proximal end portions 214b. The coupler body 214 is directly connected to a universal filter via a tri-lumen tube 204 through parallel tube fittings. The distal end portion 214a of the coupler body 214 includes a plurality of flow passages defined by four concentric annular walls. More particularly, the distal end portion 214a of coupler body 214 includes a central flow passage 222 defined by an inner annular wall 232, a medial flow passage 224 defined between a medial annular wall 234 and the inner annular wall 232, and an outer flow passage 226 defined between an outer annular wall 236 and the medial annular wall 234.

Figure 2:
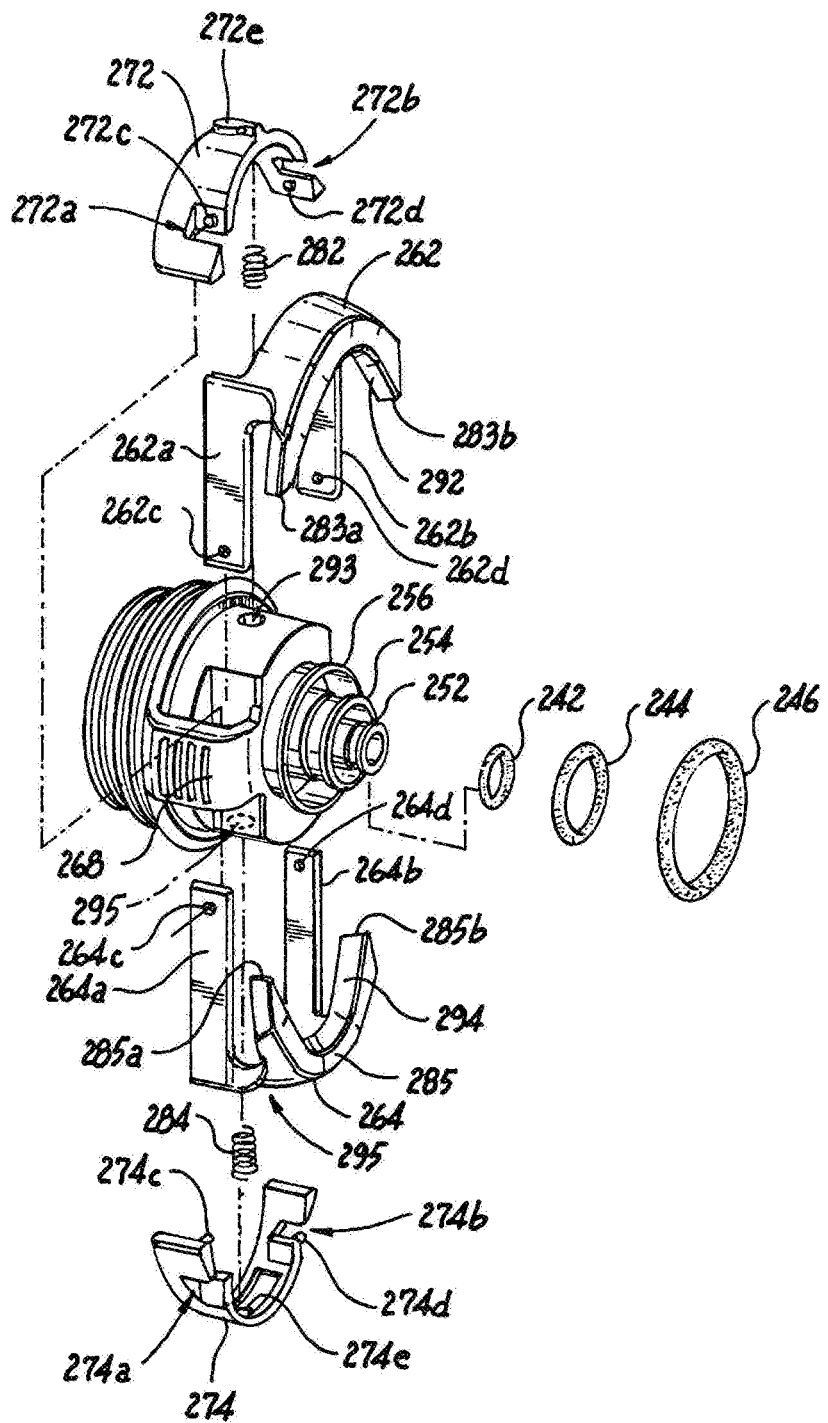
FIG. 2 is an exploded perspective view of the coupler of FIG. 1, showing a plurality of O-rings and diametrically opposed latch assemblies.

A plurality of O-rings are positioned within grooves on each respective annular wall to mate the coupler body 214 with luer fittings 322 (shown in FIG. 3) of the mating device 300. The luer fittings 322 are coaxial flow passages that mate with the annular walls 232, 234, 236 and flow passages 222, 224, 226 of the coupler 200 when fully assembled. The O-rings increase manufacturability of the coupler 200 to fit with the luer fittings 322 of the mating device 300 without the need for an additional luer and still being backwards compatible to all existing products on the market. As shown in FIG. 2, a first O-ring 242 is positioned in groove 252 on an exterior portion of inner annular wall 232. Similarly, a second O-ring 244 is positioned in groove 254 on an exterior portion of medial annular wall 234 and a third O-ring 246 is positioned in groove 256 on an exterior portion of outer annular wall 236.

Figure 3:
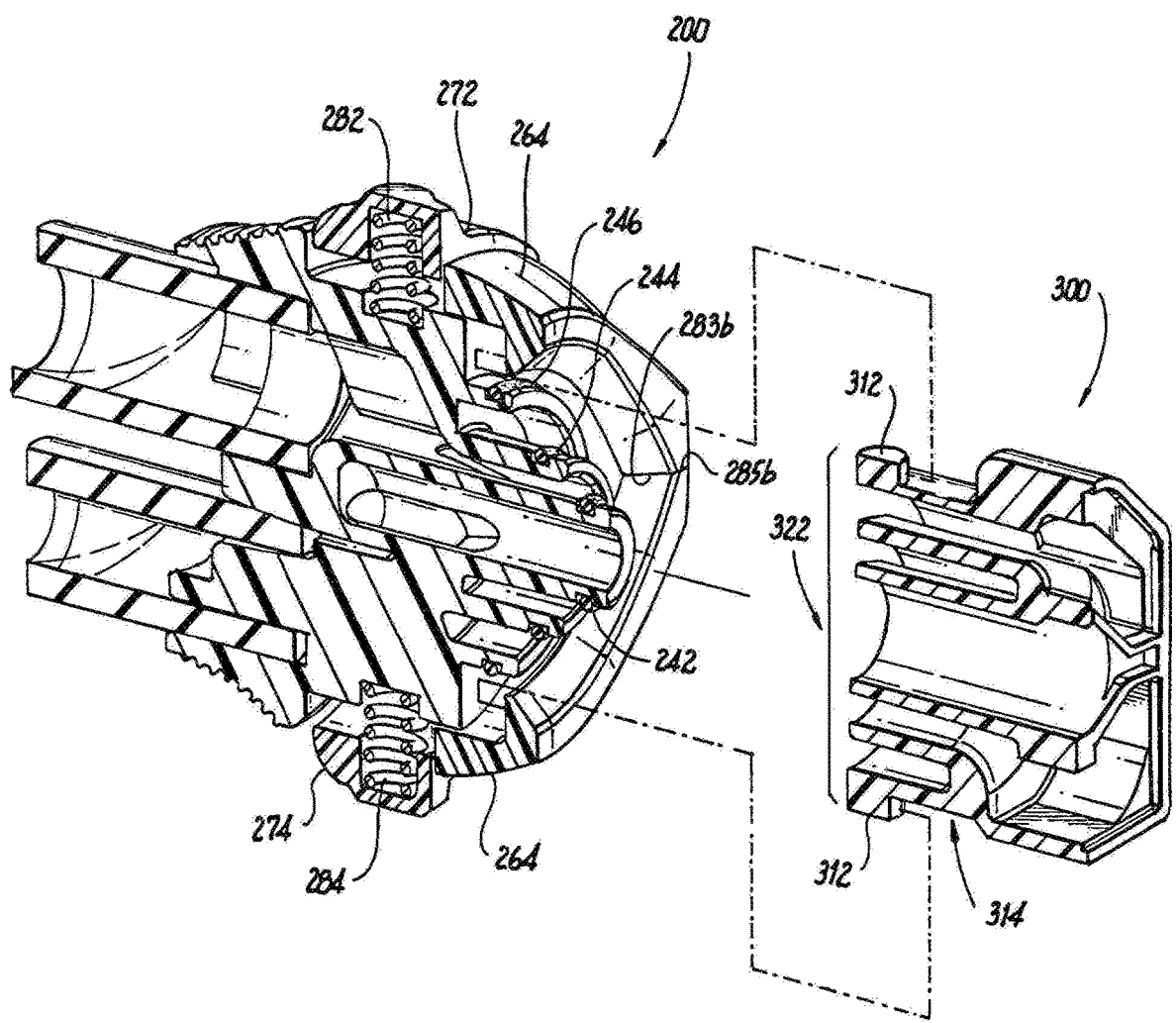
FIG. 3 is a cross-sectional view taken along line 3-3 of FIG. 1, showing the coupler and mating device.

With continued reference to FIGS. 1-3, the coupler body 214 includes several symmetrical features to join coupler 200 with the mating device 300. The symmetrical features include two diametrically opposed latch assemblies including latches 262, 264 and caps 272, 274. Two springs 282, 284 allow the latches 262, 264 to be spring loaded and easily maneuverable with the matching device 300. The latches 262, 264 are generally semi-circular housings positioned on the distal end 214a of the coupler body 214.

Figure 4:
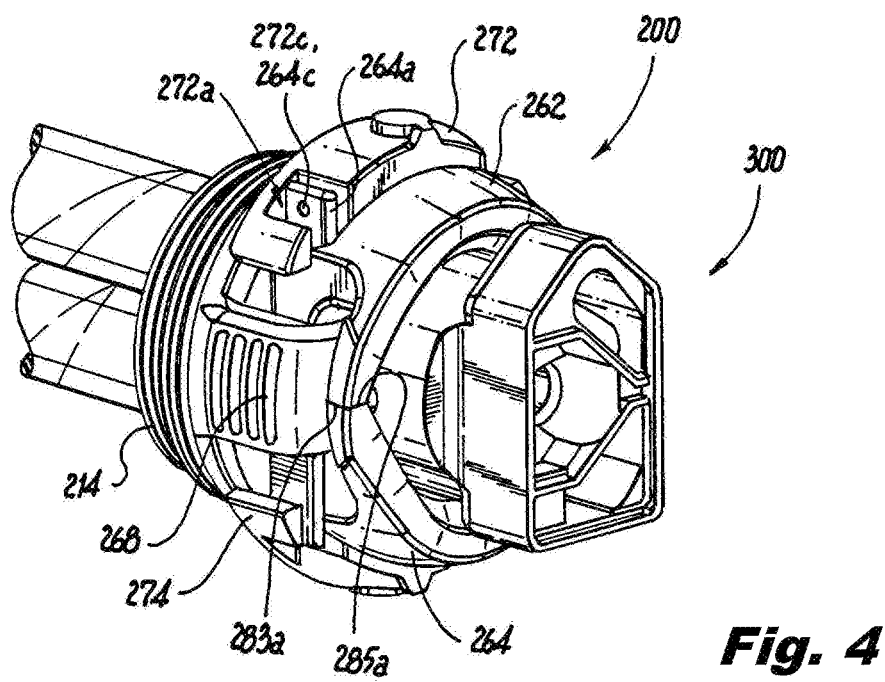
FIG. 4 is a perspective view of the coupler and mating device attached thereto.

Each latch 262, 264 includes two outwardly extending parallel extensions 262a, 262b, 264a, 264b which slideably engage within slots 268 of the coupler body 214. As shown in FIG. 4, when assembled, the extensions are juxtaposed within the slots such that extensions 264a and 264b are inboard of extensions 262a and 262b, respectively. Each latch 262, 264 also includes a locking feature 283, 285 that fully enclose the annular walls and mating device when the coupler 200 is joined with the mating device 300. Ends 283a, 283b, 285a, 285b of the locking features 283, 285 are adjacent one another when the coupler 200 and mating device 300 are joined. In other words, ends 283a and 285a are adjacent one another and ends 283b and 285b are adjacent one another when fully assembled. Additionally, each locking feature 283, 285 includes a cam face 292, 294, respectively, that mates with external surface 314 of mating device to hold the coupler 200 in place.

Caps 272, 274 are designed to easily fit tightly with latches 262, 264 while also manipulating the springs 280, 282. Each cap 272, 274 includes notches 272a, 272b, 274a, 274b with posts 272c, 272d, 274c, 274d which engage holes 262c, 262d, 264c, 264d of each respective extension 262a, 262b, 264a, 264b. For example, as shown in FIG. 4, extension 264a is positioned within notch 272a of cap 272 with post 272c within hole 264c. Each cap further includes spring pockets 272e, 274e to contain the springs 282, 284 between the caps 272, 274 and corresponding spring holes 293, 295 of coupler body 214.

Figure 5:
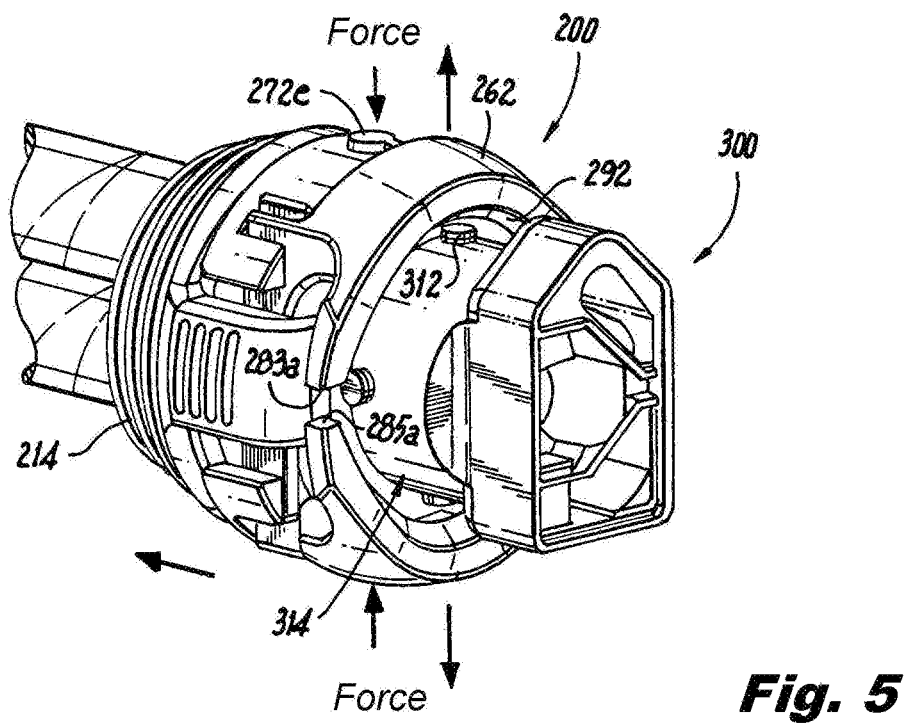
FIG. 5 is a perspective view of the coupler and mating device, showing removal of the coupler from the mating device.

With reference to FIGS. 4 and 5, the coupler 200 and mating device 300 can be easily joined by simply pushing the coupler 300 against radially outward extending posts 312 of the mating device 300. More specifically, cam faces 292, 294 push up against posts 312 such that the O-rings 242, 244, 246 begin to engage the luer fittings 322 of the mating device 300. Continuing to push the coupler 200 towards the mating device 300 begins to cam the locking features 283, 285 up and over the posts 312 onto the mating device 300. Once the coupler 200 is fully pushed onto the mating device 300, the cam faces 292, 294 are locked into position resting against surface 314 of the mating device 300.

Ends 283a, 283b, 285a, 285b are adjacent such that the latches 262, 264 fully encloses a portion of mating device 300. At this point, if the tubing 204 twists, the coupler 200 can twist around the mating device 300 and not pull off.

With reference to FIG. 5, the coupler 200 can be easily removed from the mating device 300 by pressing down on both spring pockets 272e, 274e to compress springs 282, 284 and separate the locking features 283, 285. More specifically, as the springs 282, 284 are compressed, locking features 283, 285 begin to separate. This in turn allows ends 283a, 285b to be pulled away from one another. Once the locking features 283, 285 are separated, the coupler 200 can be removed from the mating device 300 by simply pulling the coupler 200 away from and off of the mating device 300.

Alternate embodiments of the coupling assembly are shown and described herein. Couplers and mating devices described in detail below include similar features to coupler 200 and mating device 300 therefore similar reference numerals are shown to identify similar features and will not be described in additional detail.

Referring to FIGS. 6-8, an alternate embodiment of coupling assembly 600 includes coupler 700 having caps 772, 774 with flexible tabs 796, 798, respectively, which engage with mating device 800 and hold coupler 700 in place. More specifically, flexible tabs 796, 798 extend outwardly from the caps 772, 774 in a generally "V" shape and rest adjacent a respective flat surface 776, 778 of coupler body 614 when coupler 700 and mating device 800 are disassembled.

As coupler body 714 is pushed towards and onto mating device 800 the flexible tabs 796, 798 separate or flex away from coupler body 714 when in contact with posts 812. With continued pressure, ends 783a, 785a and 783b, 785b are driven apart from one another allowing coupler 700 to be pushed over posts 812 and flexible tabs 796, 798 are secured along surface 814 of mating device 800. The coupler body 714 is released from the mating device 800 by pressing on caps 772, 774 which causes the flexible tabs 796, 798 to separate ends 783a, 785a and 783b, 785b allowing the coupler 700 to be pulled away from and off of mating device 800.

With reference to FIGS. 9-12 an alternate embodiment of coupling assembly 900 is shown having a coupler 1000 with cantilever arms 1072, 1074 extending from symmetrical latches 1062, 1064, respectively. Latches 1062, 1064 include extensions 1062a, 1062b, 1064a, 1064b, respectively, that slideably engage with coupler body 1014 through openings 1068. Two openings 1068 are shown in FIG. 9 to accept extensions 1062a and 1064a therethrough. Each extension 1062a, 1062b, 1064a, 1064b include ratchet teeth 1062c, 1062d, 1064c, 1064d, respectively, that lock the latches 1062, 1064 together. For example, as shown in FIG. 11, ratchet teeth 1062c and 1064c are locked together when latches 1062, 1064 are in a locked position.

Cantilever arms 1072, 1074 extend proximally from the latches 1062, 1064 and are used as fulcrums for removing the coupler body 1014 from the mating device 1100. To engage the coupler 1000 with the mating device 1100, the coupler 1000 is pushed onto the mating device 1100 until cam faces 1092, 1094 on the latches 1062, 1064 are pushed over posts 1112 until the cam faces are locked onto surface 1114 of the mating device 1100. To remove (shown in FIG. 12), pressing the cantilever arms 1072, 1074 towards coupler body 1014 releases the ratchet teeth 1062c, 1062d, 1064c, 1064d and causes locking features 1083, 1085 to separate such that the ends 1083a, 1085a and ends 1083b, 1085b separate allowing coupler 1000 to be pulled away from and off of mating device 1100.

Figure 13:
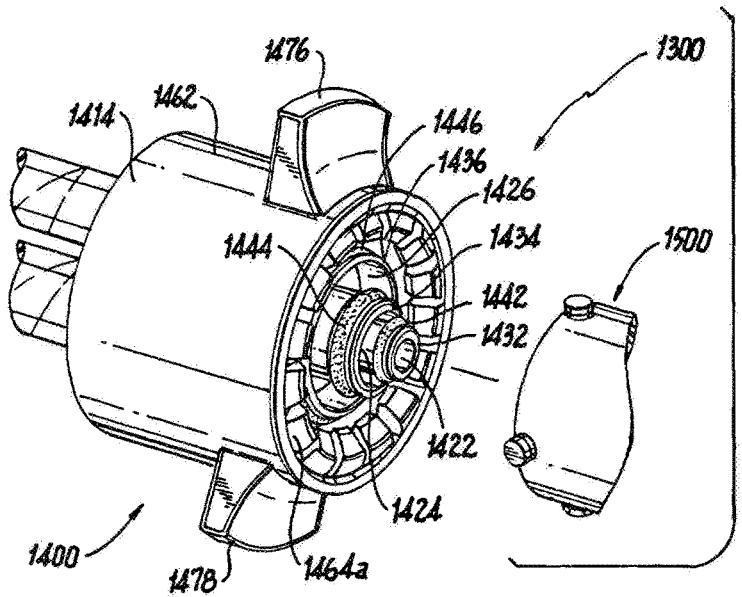
FIG. 13 is a perspective view of an alternate embodiment of a coupling assembly for a tri-lumen tube set, showing a coupler and a mating device.
Figure 14:
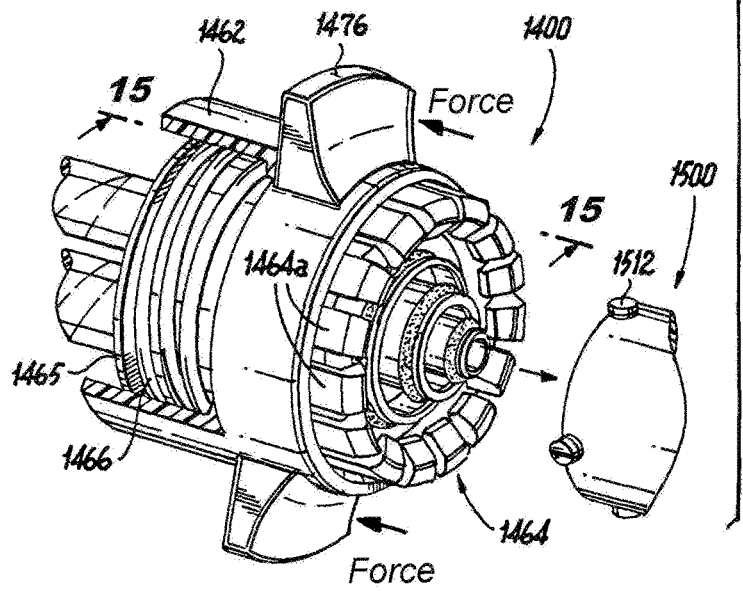
FIG. 14 is a perspective view illustrating an outer sleeve of the coupler of FIG. 13 in a proximal position exposing circumferentially arranged flexible fingers of an inner sleeve.
Figure 15:
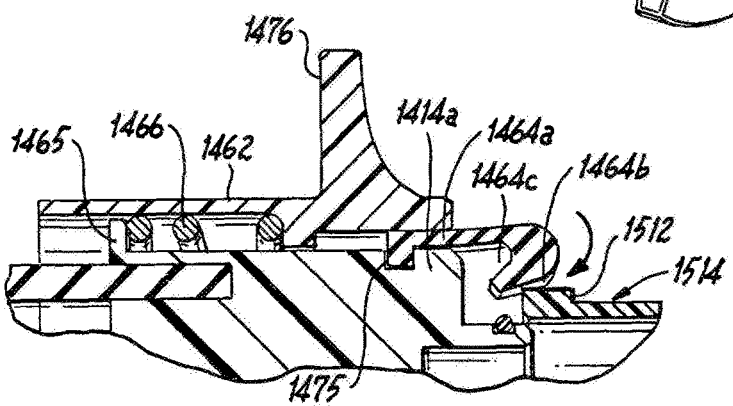
FIG. 15 is a cross-sectional view taken along line 15-15 of FIG. 14, showing the flexible fingers engaging with the mating device.
Figure 16:
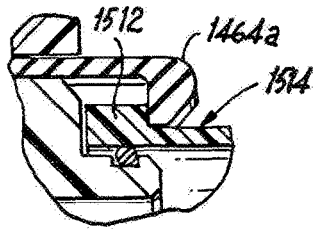
FIG. 16 is a side view showing the flexible fingers of the inner sleeve locked with posts of the mating device.
Figure 17:
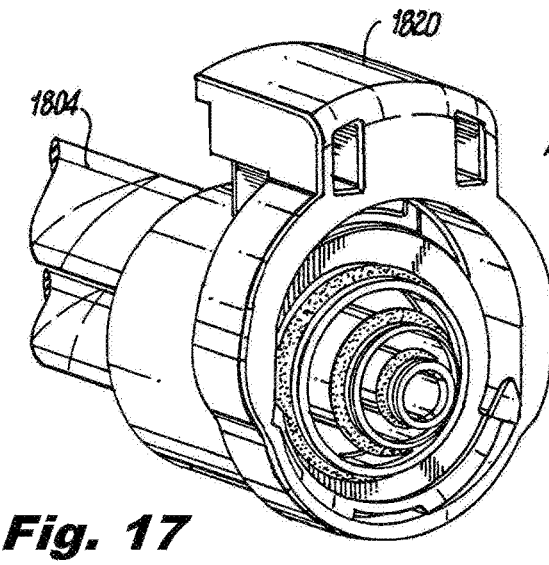
FIG. 17 is a perspective view of an alternate embodiment of a coupling assembly for a tri-lumen tube set, showing a coupler.

Referring to FIGS. 13-15 a further embodiment of coupling assembly 1300 is shown. Coupler body 1414 includes a spring loaded outer sleeve 1462 encircling an inner sleeve 1464. The inner sleeve 1464 includes a plurality of circumferentially arranged flexible fingers 1464a which surround annular walls 1432, 1434, 1436, O-rings 1442, 1444, 1446 and flow passages 1422, 1424, 1426 of the coupler 1400. An annular groove 1475 (shown in FIG. 15) is included on the distal end 1414a of the coupler body 1414 which locks the inner sleeve 1464 with the coupler body 1414. When the outer sleeve 1462 is in a distal position (shown in FIG. 13) the inner sleeve 1464 is secured therein and the flexible fingers 1464a are in a locked position. A flange 1465 of the coupler body 1414 maintains at least one spring 1466 in position between the coupler body 1414 and outer sleeve 1462.

To engage the coupler 1400 with the mating device 1500, handles 1476, 1478 of the outer sleeve 1462 are pulled proximally (shown in FIG. 14) to expose the flexible fingers 1464a. The coupler 1400 is then pressed onto the mating device 1500 and cam faces 1464b on the flexible fingers 1464a cam up and over the posts 1512 (shown best in FIG. 15) until a hook feature 1464c of the flexible fingers 1464a is locked onto posts 1512 (shown best in FIG. 16). The outer sleeve 1462 is released distally which once again covers the inner sleeve 1464 and secures the flexible fingers 1464a. To remove, the outer sleeve 1462 is pulled to the proximal position and the flexible fingers 1464a are exposed to allow the coupler 1400 to be pulled away from and off of mating device 1500.

Figure 18:
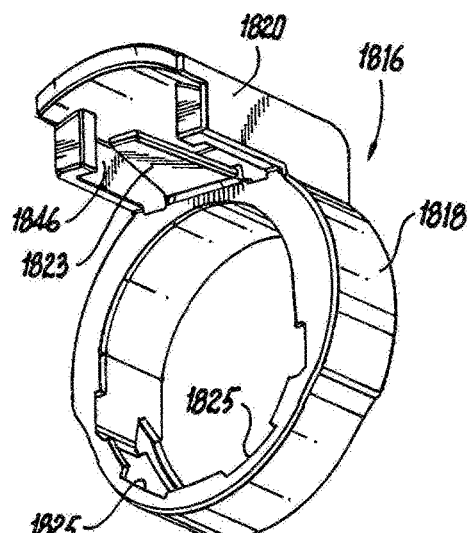
FIG. 18 is a perspective view of a ring assembly associated with the coupler having a disc attached a flexible arm.
Figure 19:
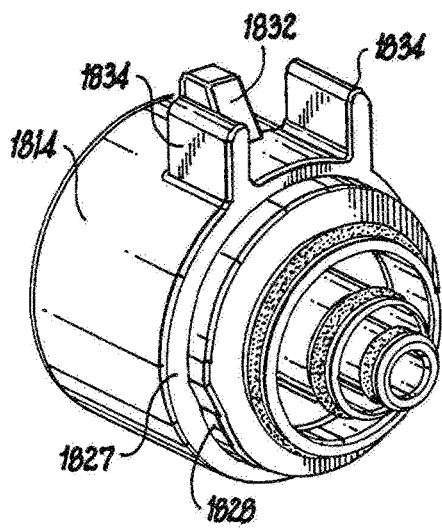
FIG. 19 is a perspective view of the coupler of FIG. 17, showing an external post and two anchors to engage with the ring assembly.

FIGS. 17-20 illustrate an additional embodiment of coupling assembly 1700 with coupler 1800 and mating device 1900. FIG. 18 shows a ring assembly 1816 which locks with coupler body 1814 and maintains a tight seal. The ring assembly 1816 includes a disc 1818 and an arm 1820 extending outwardly perpendicular from the disc 1818. Coupler body 1814 includes an external post 1832 and two anchors 1834 to engage the arm 1820 and prevent disc 1818 from moving linearly towards the mating device 1900, but allows vertical movement of the disc 1818 in relation to coupler body 1814.

Coupler body 1814 also includes an annular external groove 1827 (shown in FIG. 19) to hold the disc 1818 in position and additional features (e.g., notches and grooves) 1828 (shown in FIG. 18) that correspond to related features 1825 of the disc 1818 such that the disc 1818 fits securely with coupler body 1814. The arm 1820 extends proximally from the disc 1818 and includes generally "L" shaped openings 1846 which attach to the anchors 1834 of the coupler body 1818 when the arm 1820 is in a compressed position. As shown in FIG. 18, a flexible tab 1823 is disposed within the arm 1820 and mates against post 1832 of coupler body 1814 when in an uncompressed position.

Figure 20:
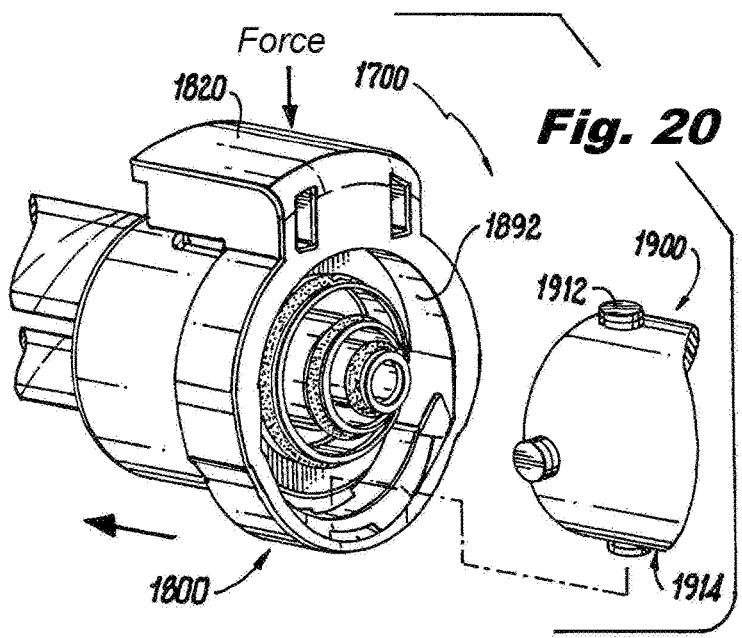
FIG. 20 is a perspective view of the coupler and a mating device, showing removal of the coupler from the mating device.

To use, the coupler 1800 is pushed into the mating device 1900 until a cam face 1892 (shown in FIG. 20) on the disc 1818 cams up and over the mating device posts 1912 and locks the disc 1818 against surface 1914 of the mating device 1900. In this position, the coupler 1800 can rotate around the mating device 1900 if the tubes 1804 from the filter are twisted. As shown in FIG. 20, pressing down on the arm 1820 causes flexible tab 1823 to press against anchor 1832 and loosen cam face 1892 from mating device. Coupler can be pulled away and off of the mating device.

II. Dual Lumen Coupling Assemblies

Figure 21:
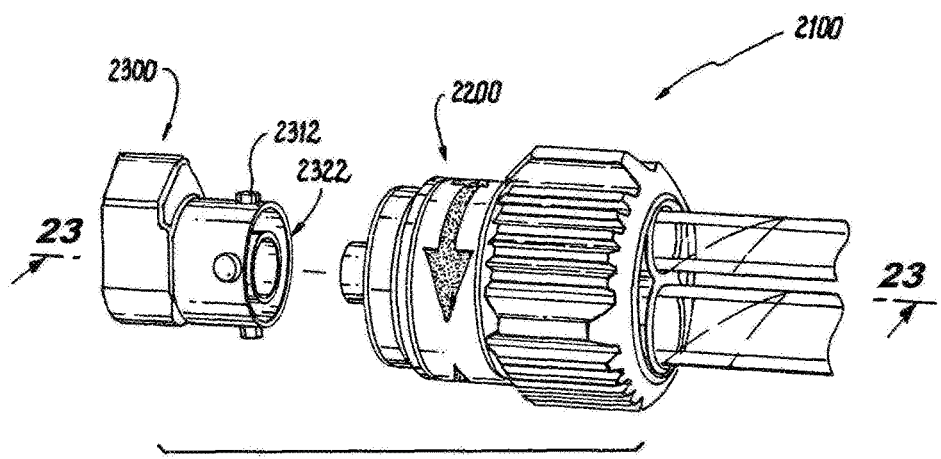
FIG. 21 is a perspective view of an alternate embodiment of a coupling assembly for a dual lumen tube set, showing a coupler and a mating device.
Figure 22:
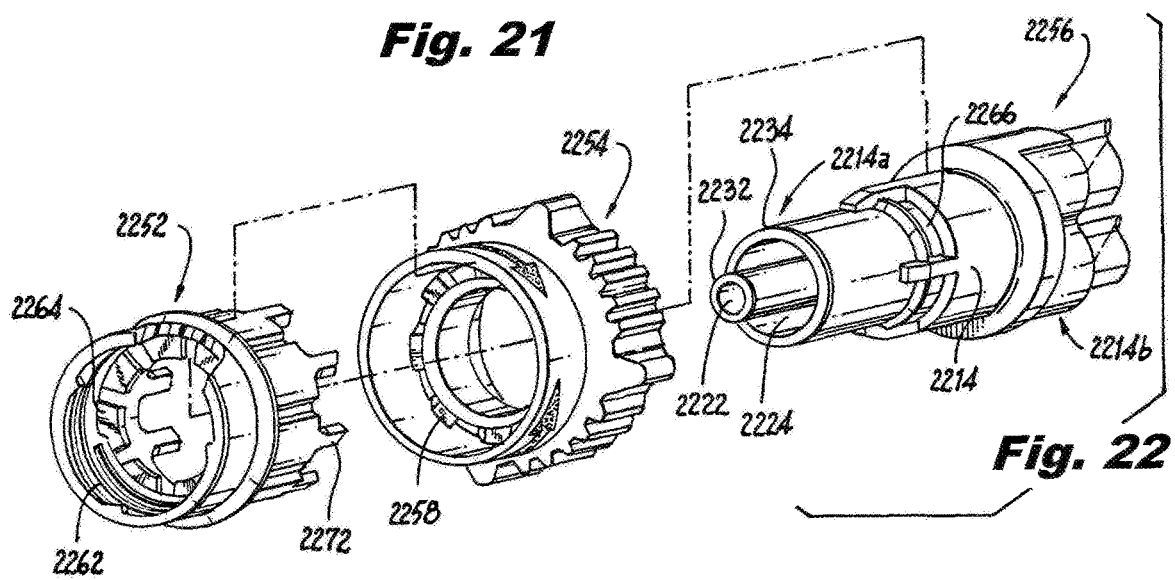
FIG. 22 is an exploded perspective view of the coupler of FIG. 21, showing a ring and a shroud.
Figure 23:
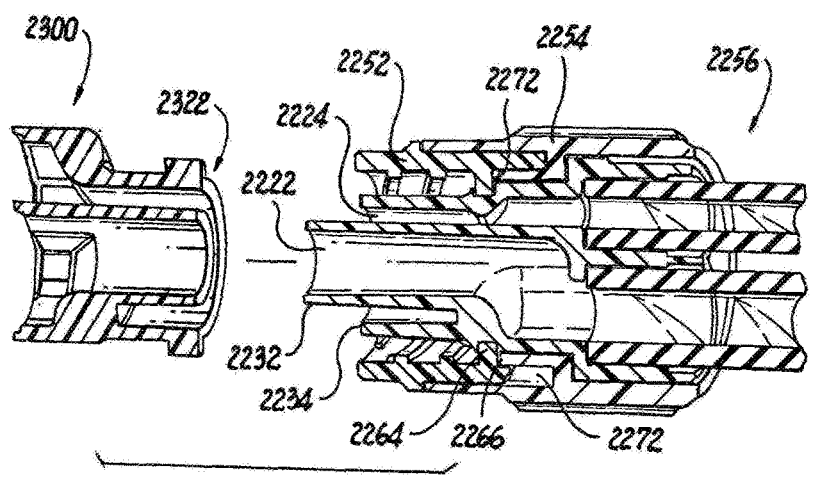
FIG. 23 is a cross-sectional view taken along line 23-23 of FIG. 21, showing an assembled coupler and the engagement between the coupler and mating device.

FIGS. 21-23 show a coupling assembly 2100 having a dual lumen coupler 2200 and a mating device 2300 with dual luer 2322 features. The coupler 2200 includes a ring 2252 and a connector 2256 both coupled to a shroud 2254. The ring 2252 and shroud 2256 are linearly aligned with an elongated generally cylindrical body 2214 of the connector 2256. The connector body 2214 includes a proximal end 2214*a* and an opposing distal end 2214*b* that couples with the shroud 2254 and ring 2252 and engages with luer fittings 2322 of the mating device 2300. The connector 2256 includes two concentric annular walls on the distal end allowing for two flow passages. Specifically, an inner annual wall 2232 defines an inner flow passage 2222 is defined by inner annular wall 2232 and outer flow passage 2224 is defined between the inner annular wall 2232 and an outer annular wall 2234.

As shown in FIGS. 22 and 23, the ring 2252 joins the connector 2256 and shroud 2254 to the mating device 2300 with internal threads 2262 that rotationally engage the mating device 2300. The ring 2252 includes tabs 2264 that snap fit into slots 2266 of the connector 2256 to restrict rotational movement therebetween. The ring 2252 further has flexible fingers 2272 which engage ramps 2258 of the shroud 2254. To attach the assembled coupler 2200 with the mating device 2300, a user first rotates the shroud 2254. Rotation of the shroud 2254 allows threads 2262 of ring 2252 to engage and lock onto posts 2312 of the mating device 2300. In addition, the shroud ramps 2258 contact the flexible fingers 2272 of the ring 2252 and when adequate torque is applied the flexible fingers 2272 ratchet off the ramps 2258 and tightly secure the luers 2322 with the annular walls 2232, 2234. To disengage, the user simply reverse rotates the shroud 2254 to release the threads 2262 of ring 2252 from the posts 2312 of mating device 2300.

Figure 24:
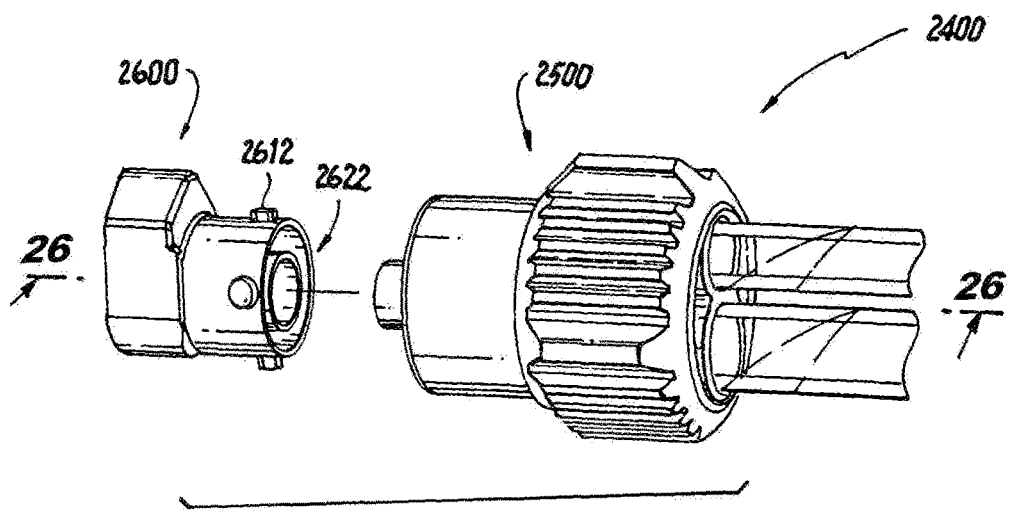
FIG. 24 is a perspective view of an alternate embodiment of a coupling assembly for a dual lumen tube set, showing a coupler and a mating device.
Figure 25:
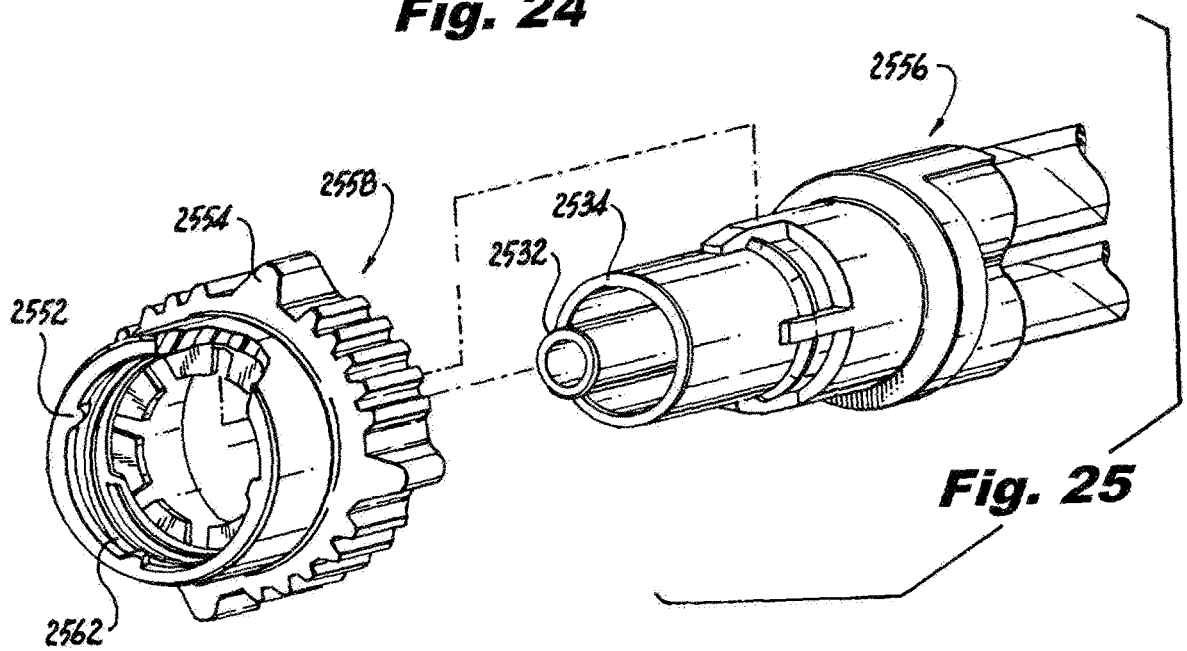
FIG. 25 is an exploded perspective view of the coupler of FIG. 24, showing a ring and shroud integrally connected.
Figure 26:
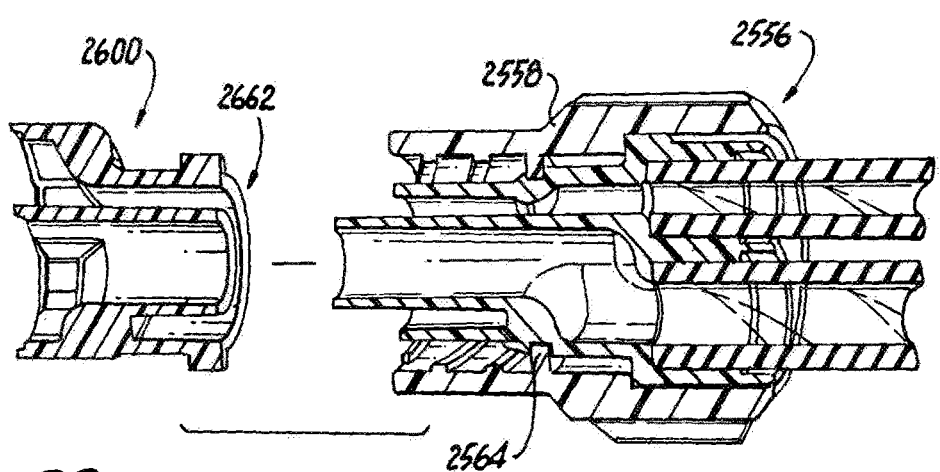
FIG. 26 is a cross-sectional view taken along line 26-26 of FIG. 24, showing an assembled coupler and alignment between the coupler and mating device.

The coupling assembly 2400 of FIGS. 24-26 is a further embodiment of a coupling assembly 2400 directed to a dual lumen coupler 2500. In this embodiment, ring 2552 and shroud 2554 are integrally combined into a single shroud assembly 2558. The shroud assembly 2558 includes internal threads 2562 (similar to threads 2262) that engage the mating device and linear snap features 2564 (similar to 2264) that attach the shroud assembly 2558 to the connector 2556. To attach the coupler 2500 to the mating device 2600, the posts 2612 of the mating device are aligned with the internal threads 2562. The shroud assembly 2558 is rotated until the annular walls 2532, 2534 of connector and the luers 2622 of mating device 2600 are attached.

III. Single Lumen Coupling Assemblies

Figure 27:
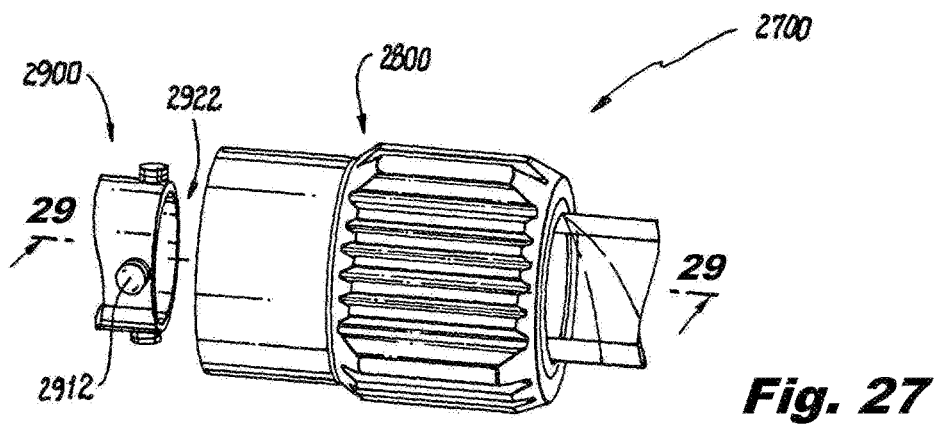
FIG. 27 is perspective view of an alternate embodiment of a coupling assembly for use with a single lumen, showing a coupler and a mating device.
Figure 28:
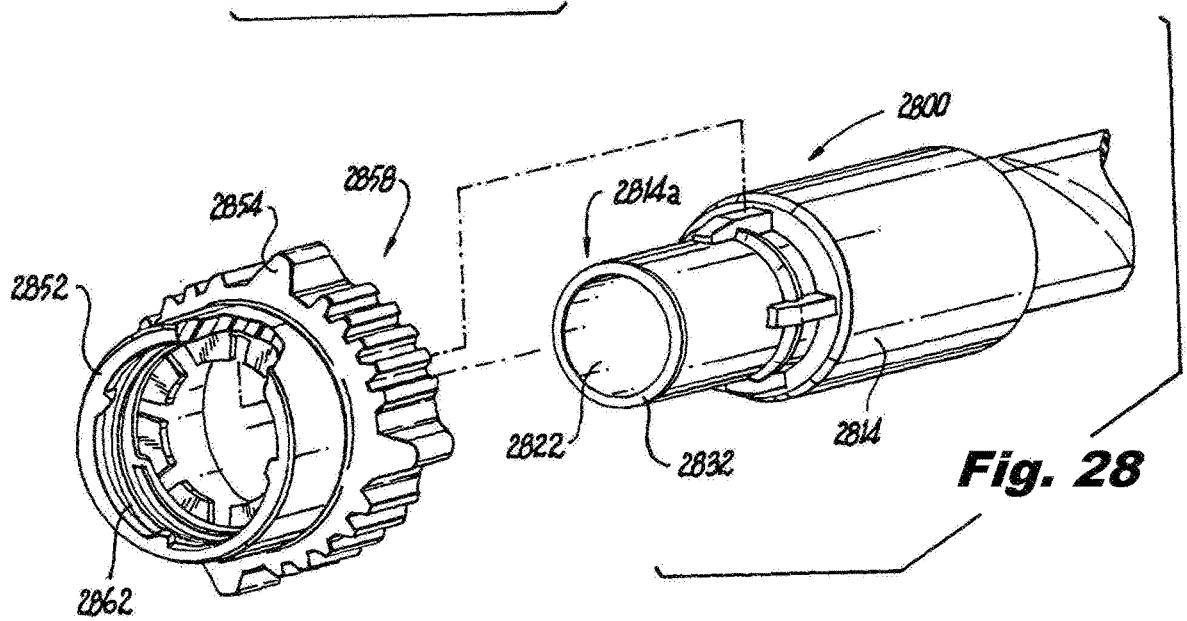
FIG. 28 is an exploded perspective view of the coupler of FIG. 27, showing a ring and shroud integrally connected.
Figure 29:
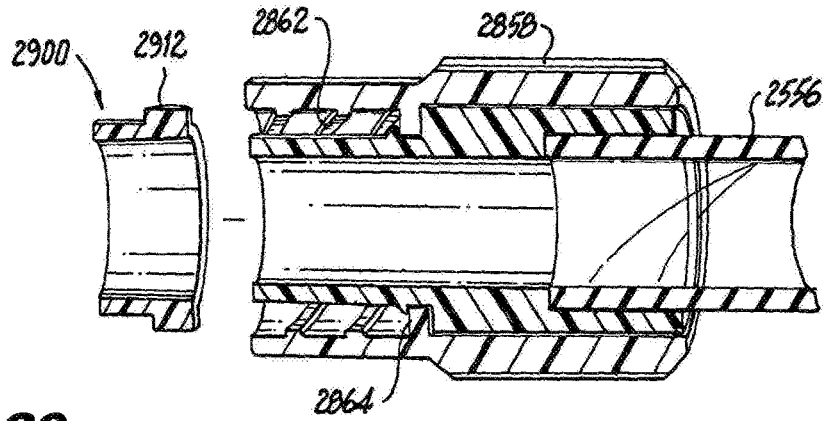
FIG. 29 is a cross-sectional view taken along line 29-29 of FIG. 27 showing an assembled coupler and alignment between the coupler and mating device.

FIGS. 27-29 illustrate a coupling assembly 2700 similar to coupling assembly 240 of FIGS. 24-26, however the connector 2800 is directed to a single lumen and the mating device 2900 includes a single luer 2922. In this embodiment, a distal end 2814*a* of the connector body 2814 includes one annular wall 2832 and one flow passage 2822. The design of the ring 2825 and shroud 2854 are the same as ring 2552 and shroud 2554 with the ring 2825 and shroud 2854 integrally connected to form a shroud assembly 2858. The shroud assembly 2858 has an internal thread 2862 that mate with posts 2912 of the mating device 2900 and linear snap features 2864 to engage distal end 2814*a* of connector. The shroud assembly 2858 is rotated until the internal thread 2862 engages mating device 2900 and the annular wall 2832 and luer 2922 fit together.

Figure 30:
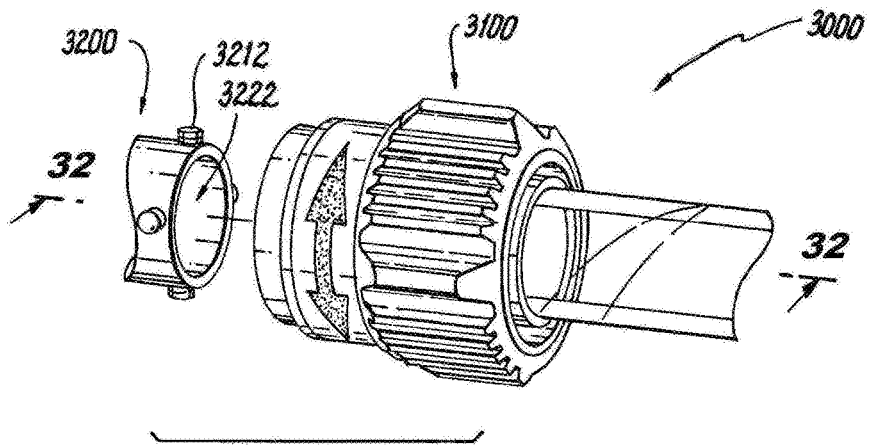
FIG. 30 is a perspective view of an alternate embodiment of a coupling assembly for use with a single lumen, showing a coupler and a mating device.
Figure 31:
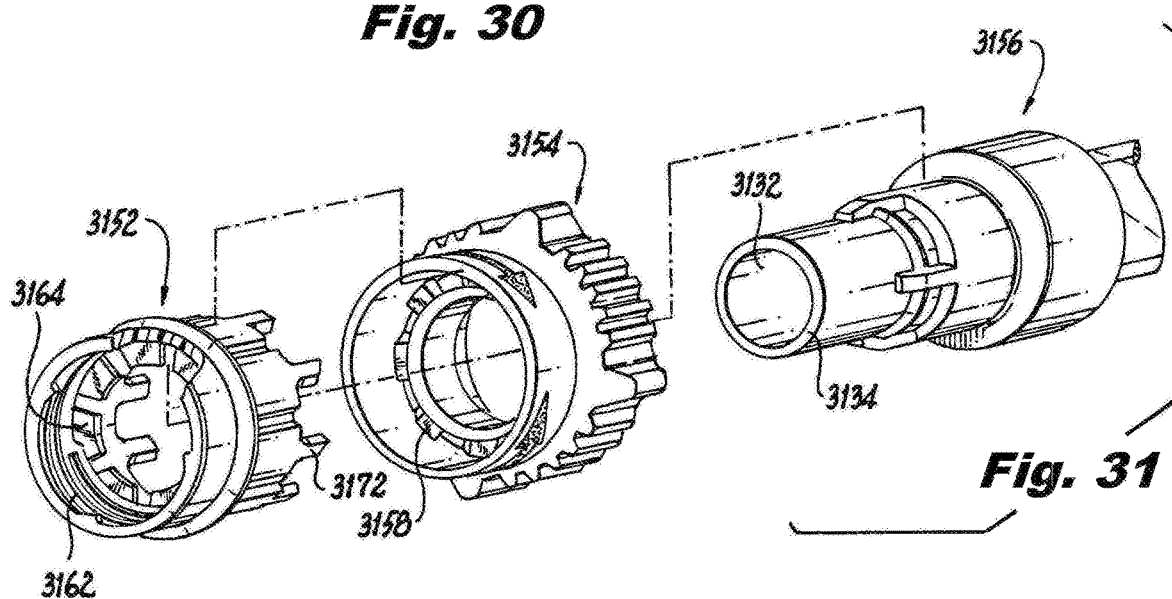
FIG. 31 is an exploded perspective view of the coupling assembly of FIG. 30, showing a ring and a shroud.
Figure 32:
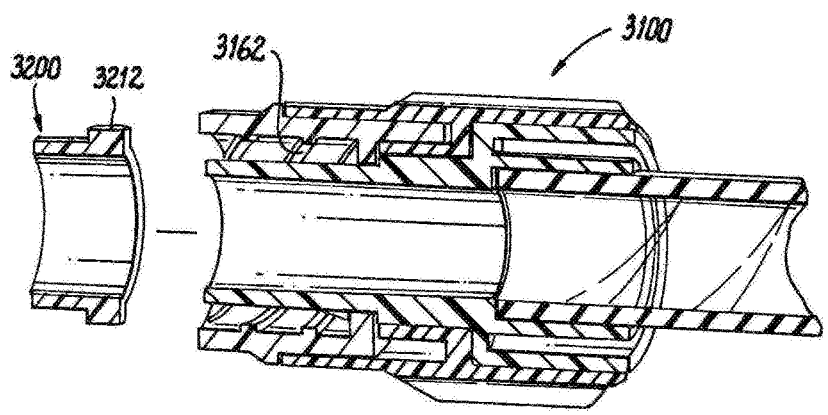
FIG. 32 is a cross-sectional view taken along line 32-32 of FIG. 30, showing an assembled coupler and alignment between the coupler and mating device.
Figure 33:
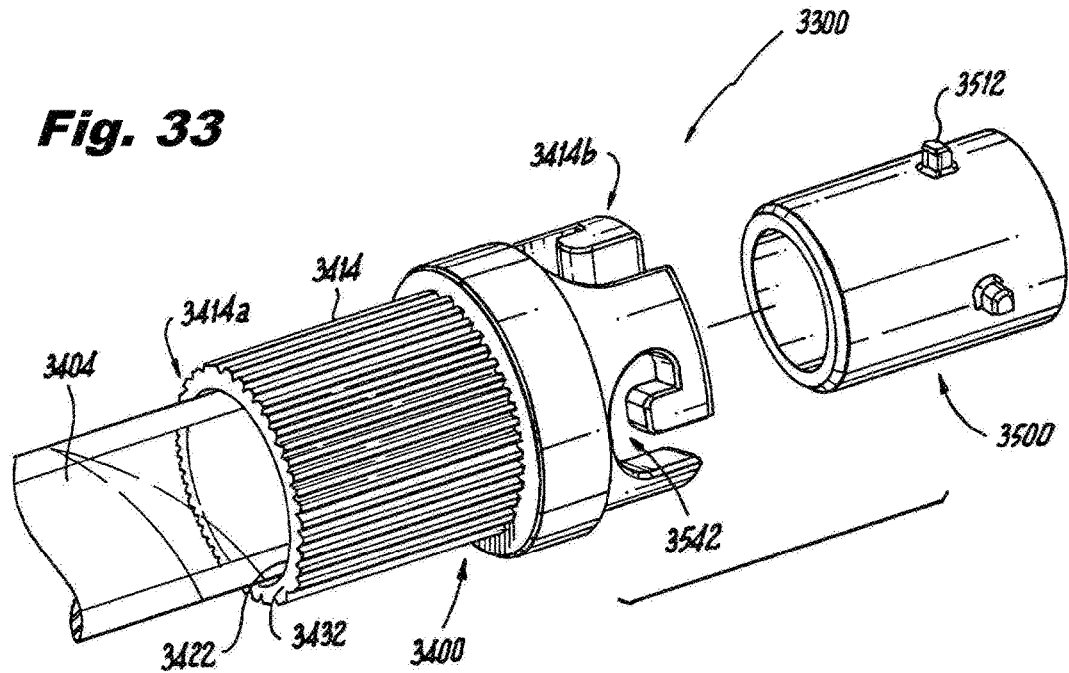
FIG. 33 is a perspective view of an alternate embodiment of a coupling assembly for use with a single lumen, showing a coupler and a mating device.
Figure 34:
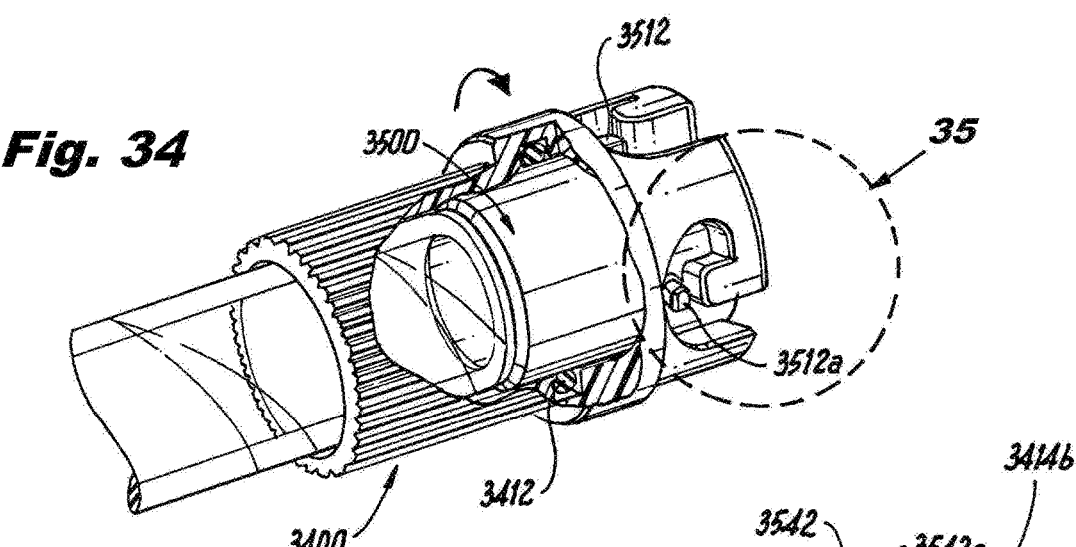
FIG. 34 is a cut-out perspective view of the coupling assembly of FIG. 33 showing rotation of the coupler to engage posts of the mating device within cam slots.
Figure 35:
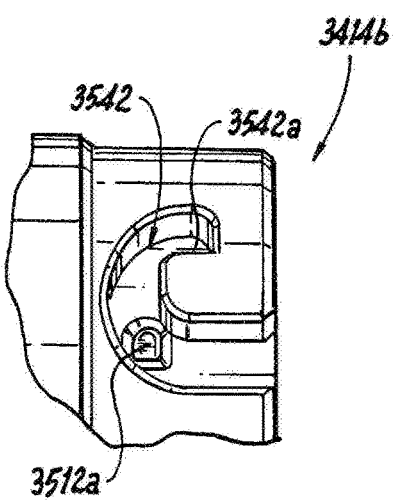
FIG. 35 is a detailed view of the cam slot of the coupler of FIG. 34.

FIGS. 30-32 illustrate a coupling assembly 3000 similar to coupling assembly 2100 as shown in FIGS. 21-23 however, the connector 3100 is directed to a single flow passage 3132 with one annular wall 3134 and the mating device includes a single luer 3222. Ring 3152 attaches to the connector 3156 with snap features 3164 to lock rotation of the connector 3156. The ring also has flexible fingers 3172 which will ratchet over ramp features 3158 within shroud 3154. Coupler 3100 engages mating device 3200 in a similar manner as coupler 2200 with an internal thread 3162 locking with posts 3212 when rotational movement is applied to shroud 3154.

Referring now to FIGS. 33-37, a coupling assembly 3300 having a coupler 3400 and mating device 3500 is shown. The coupler 3400 has a generally cylindrical body 3414 with a proximal portion 3414*a* to engage a single lumen tube 3404 and a distal portion 3414*b* to engage with a mating device 3500. The coupler body 3414 includes a single annular wall 3432 with a flow passage 3422. An internal diameter of the annular wall 3432 is greater than the tube 3404 such that the tube 3404 securely fits within the flow passage 3422 to help promote smooth gas flow. Similarly, the inner diameter of the annular wall 3432 is greater than the outer diameter of the mating device 3500 to fit securely within the flow passage 3422 such that the mating device 3500 engages with an O-ring 3412 positioned within the coupler body 3414.

The distal end 3414*b* of the coupler body 3414 includes a plurality of cam slots 3542 to engage with posts 3512 of mating device 3500. The posts 3512 have a generally flat surface 3512*a* to mate with a corresponding flat end 3542*a* of the cam slots 3542. However, variations of the posts geometry are also contemplated, such as circular posts. In addition, further embodiments of the coupler and mating device can include variations in the number of posts and corresponding cam slots.

To attach the coupler 3400 to the mating device 3500, the mating device 3500 is first inserted into the flow passage 3422 with the cam slots 3542 and posts 3512 aligned. The mating device 3500 is pushed through the flow passage 3422 until the external wall of the mating device 3500 makes contact with the O-ring 3412. Continued pressure of the mating device 3500 into the coupler 3400 will begin to push posts 3512 to enter the cam slots 3512. The coupler 3400 is rotated with continued pressure such that the posts 3512 are fully rotated within the cam slots 3542 and the posts 3512 are in a locking position with the cam slots 3542 (shown in FIGS. 36 and 37). In the locking position, the coupler 3400 will resist pulling off or un-screwing until removal.

To remove, the coupler 3400 and mating device 3500 are again pushed towards each other and reverse rotated to direct the posts 3512 around the respective cam slot 3542. This movement will release the posts 3512 from the cam slots 3542 and the coupler 3400 and mating device 3500 are pulled away from each other. As shown in FIGS. 33-37, cam slots 3542 have a generally "U" shaped configuration to lock posts therein. However, other similar designs can be utilized. For example, as shown in FIG. 38 an alternate design for a cam slot 3842 is illustrated. The design intent for coupler body 3814 is for the cam slot 3842 to direct the posts to the end of the cam slot 3842b where the post 3512 will be restricted from pulling or rotating off until a user again pushes the coupler body 3814 towards mating device 3500 and begins reverse rotation for removal.

Figure 39:
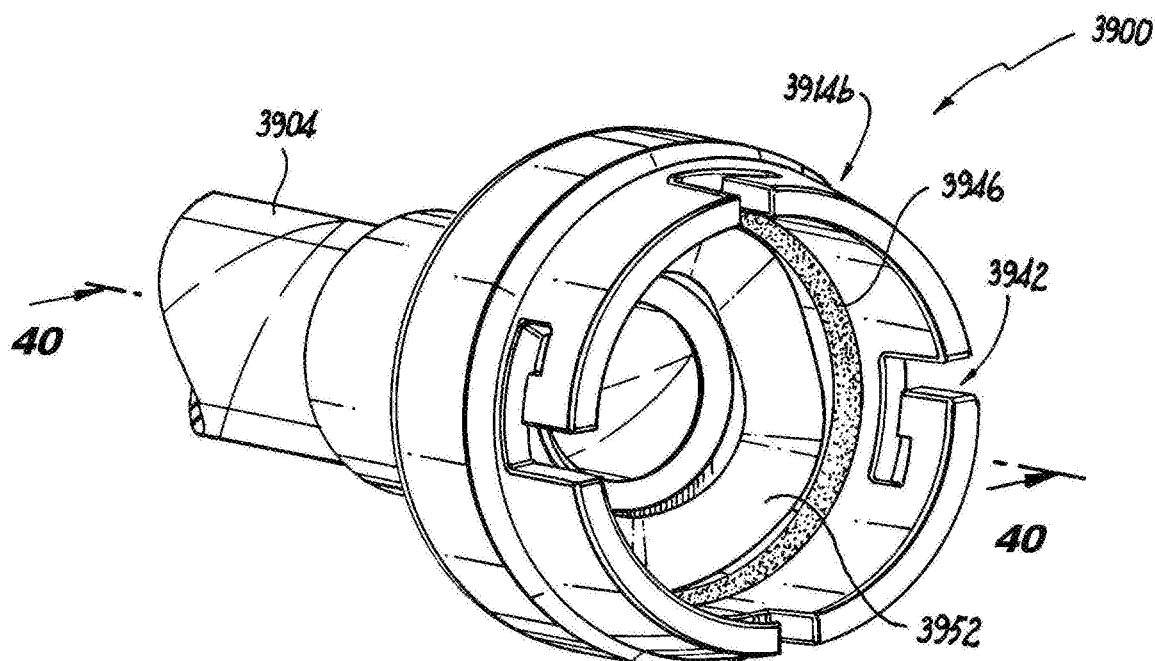
FIG. 39 is an alternate embodiment of a coupler for use with a single lumen.
Figure 40:
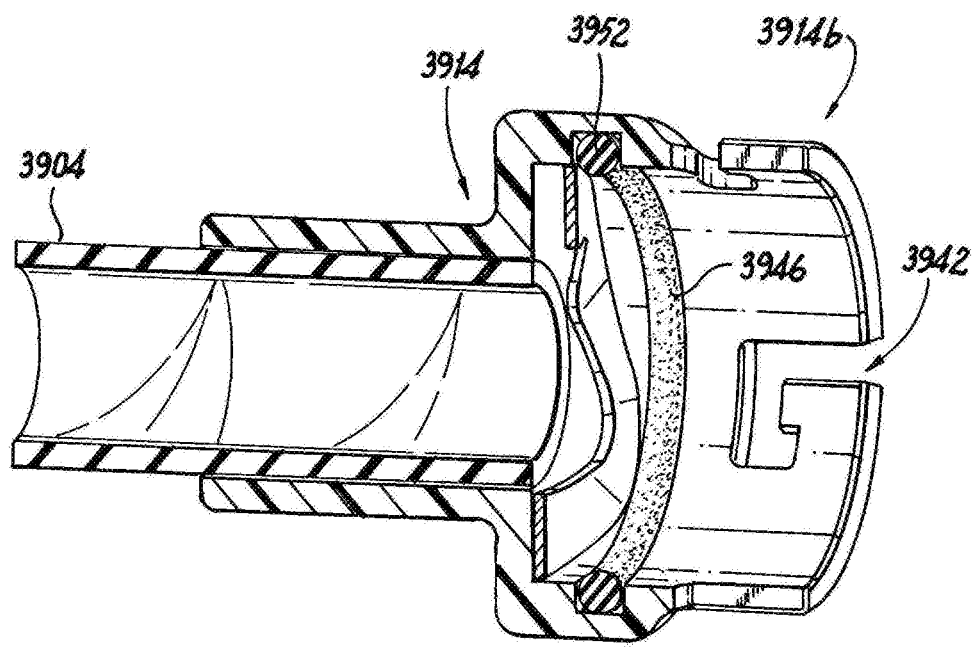
FIG. 40 is a cross-sectional view taken along line 40-40 of FIG. 39, showing a spring wave washer of the coupler body.

FIG. 39 shows an alternate embodiment of a coupler 3900. Coupler 3900 is similar to coupler 3400 in that coupler 3900 is designed for a single lumen tube 3904 and includes cam slots 3942 along a distal end 3914b of coupler body 3914. Coupler 3900 includes a compression spring 3952 positioned within coupler body 3914 proximal of an O-ring 3946. The compression spring is shown as wave washer 3952 that contacts a mating device (e.g., mating device 3500) and creates spring loaded resistance to coupler removal when the posts (e.g., posts 3512) are in a locked position (shown in FIG. 37) of the coupler cam slot 3942.

Figure 41:
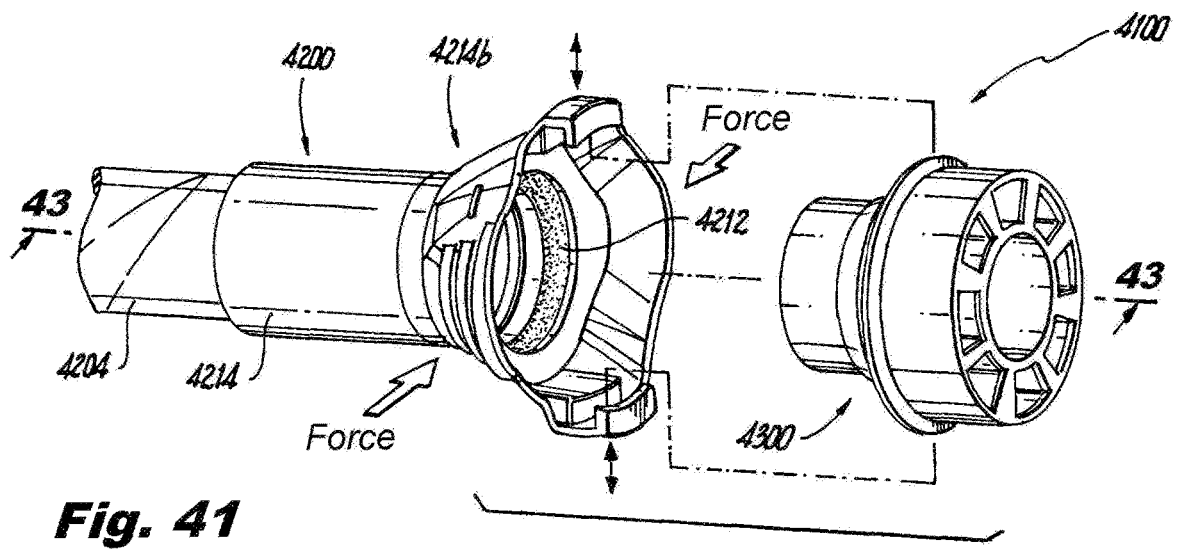
FIG. 41 is a perspective view of an alternate embodiment of a coupling assembly for use with a single lumen, showing a coupler having locking tabs for assembling and disassembling the coupler with a mating device.
Figure 42:
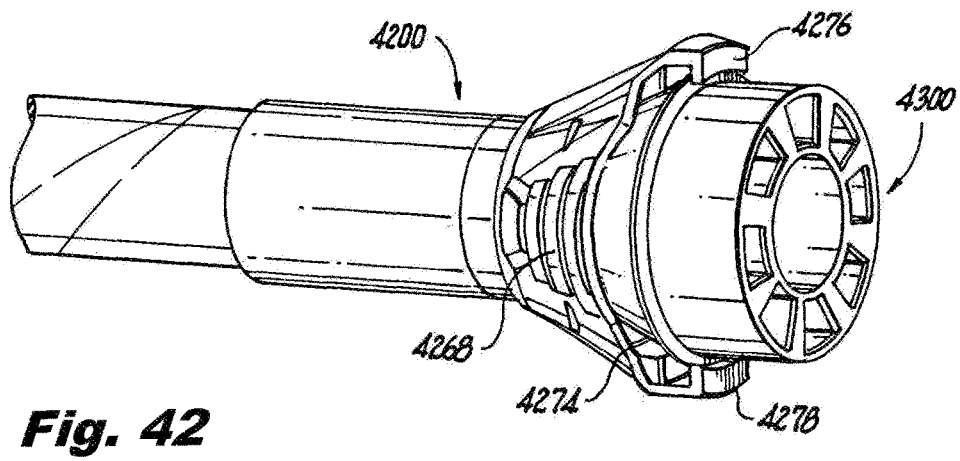
FIG. 42 is a perspective view of a coupler of FIG. 41, showing the locking tabs positioned over an annular lip of the mating device.
Figure 43:
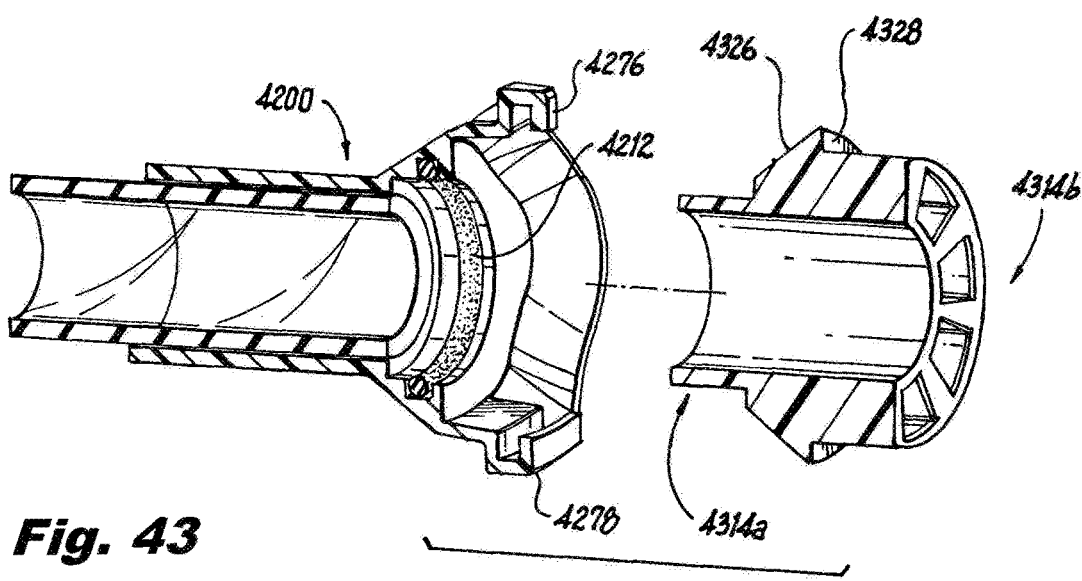
FIG. 43 is a cross-sectional view taken along line 43-43 of FIG. 41, showing alignment between the coupler and mating device.

FIGS. 41-42 illustrate an alternate embodiment of a coupling assembly 4100 including a coupler 4200 and mating device 4300. Coupler 4200 includes an O-ring 4212 to secure and seal mating device 4300 to coupler 4200. In this embodiment, inside diameter of the mating device 4300 is larger than the inside diameter of the tube 4204 to help gas flow. A further alternate embodiment would have the inside diameter the same for both the tube and mating device, similar to coupling assembly 3300 shown in FIG. 33.

As shown in FIG. 42, a distal portion 4214b of the coupler body 4214 is generally conical with a least two flexible tabs 4276, 4278 extending from an outer edge 4274. The distal portion 4214b further includes external ridges 4268 for maneuvering tabs 4276, 4278. A distal portion 4314b of the mating device has a greater external diameter than a proximal portion 4314a and includes an annular lip 4328. A ramp feature 4326 guides the flexible tabs 4276, 4278 towards the annular lip 4328. As a user pushes the coupler 4200 towards the mating device 4300 the flexible tabs 4276, 4278 flex outwardly along the ramp feature 3526 and then snap onto the lip 4328 securing the coupler 4200 to the mating device 4300. To remove, the user squeezes the external ridges 4268 to expand the flex tabs 4276, 4278 away from and off the lip 4328 and pulls the coupler 4200 away from the mating device 4300.

Figure 44:
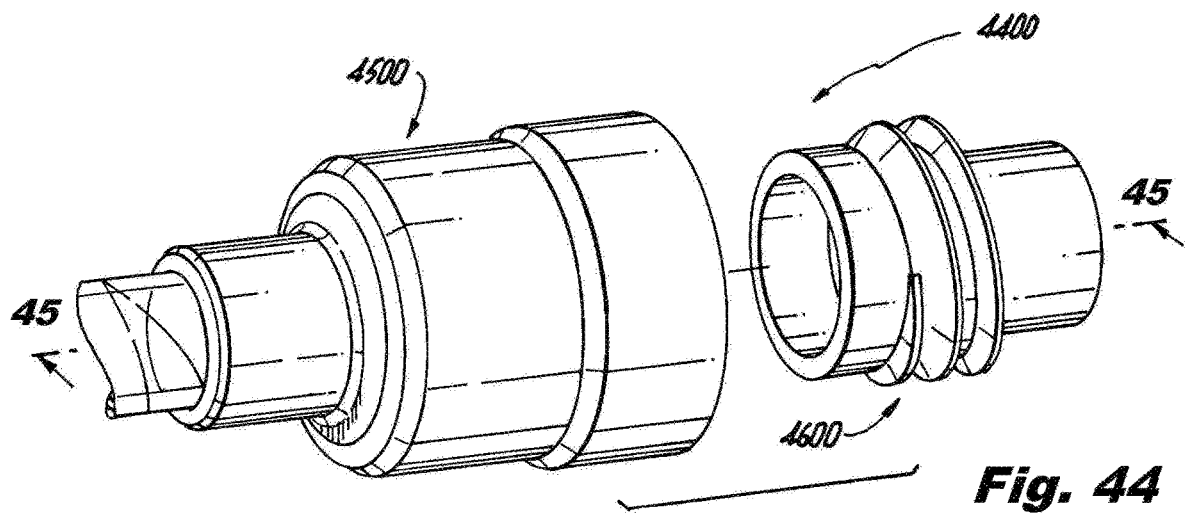
FIG. 44 is a perspective view of alternate embodiment of a coupling assembly for use with a single lumen, showing a coupler and a mating device.
Figure 45:
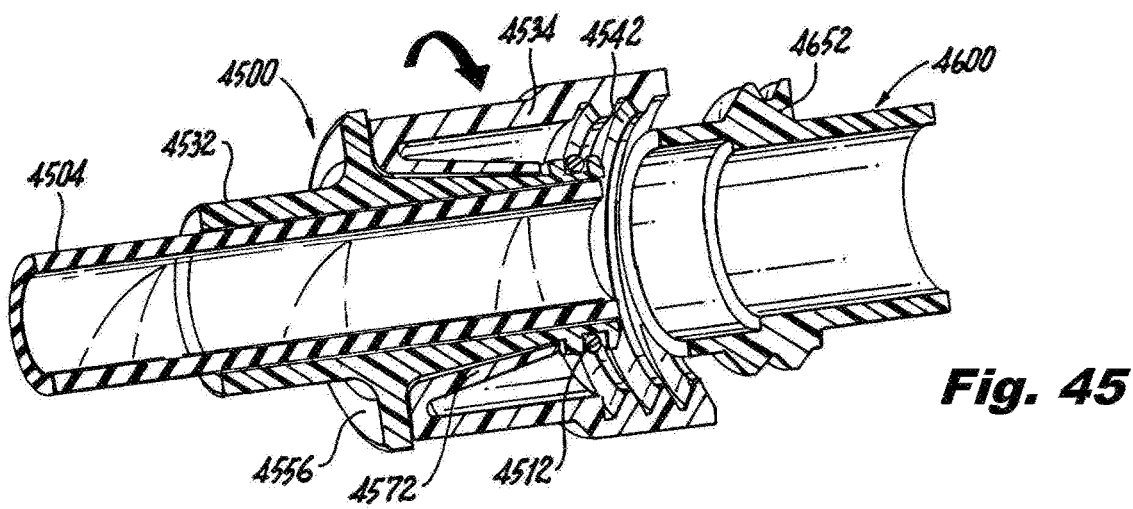
FIG. 45 is a cross-sectional view of the coupler and mating device taken along line 45-45 of FIG. 44, showing the coupler with internal threads to engage external threads of the mating device.
Figure 46:
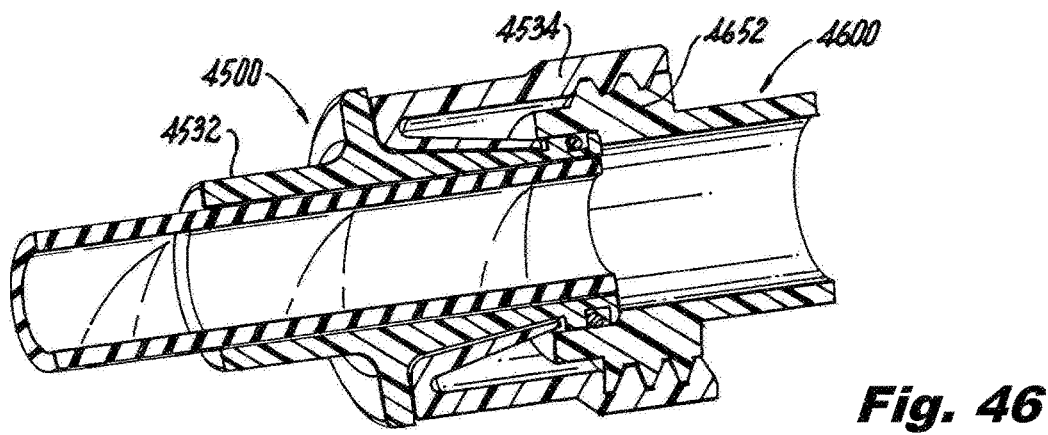
FIG. 46 is a cross-sectional view of the assembled coupler and mating device of FIG. 44.

FIGS. 44-49 illustrate alternate embodiments of coupling assemblies 4400 and 4700 with couplers 4500 and 4800 and mating devices 4600 and 4800, respectively, using threading on both the couplers 4500 and 4800 and mating devices 4600 and 4800. In FIGS. 44-45, the coupler 4500 has an inner 4532 and outer sleeve 4534. The outer sleeve 4534 includes flexible features 4572 that snap onto corresponding features 4556 of the inner sleeve 4532 during assembly. For example, as shown in FIG. 45, outer sleeve has flexible tabs 4572 that are disposed adjacent inner sleeve 4532 and rest on ledge 4556 to prevent linear movement of outer sleeve 4534. The inner sleeve 4532 is static to the lumen 4504 and the outer sleeve 4534 is allowed to rotate freely.

As shown in FIG. 45, an O-ring 4512 is secured around the inner sleeve 4532 for sealing the coupler 4500 to the mating device 4600. Outer sleeve 4534 includes internal threads 4542 that engage external threads 4652 of mating device 4600. Simply aligning the outer sleeve 4534 with the mating device 4600 and rotating the mating device 4600 into the outer sleeve 4534 intimately engages the coupler 4500 with mating device 4600. This embodiment is designed such that tubing itself does not rotate when installed. Additionally, as shown in FIG. 45, the external diameter of tube 4504 is less than the luer fitting of the mating device 4600 but could be the same, as shown in earlier embodiments.

Figure 47:
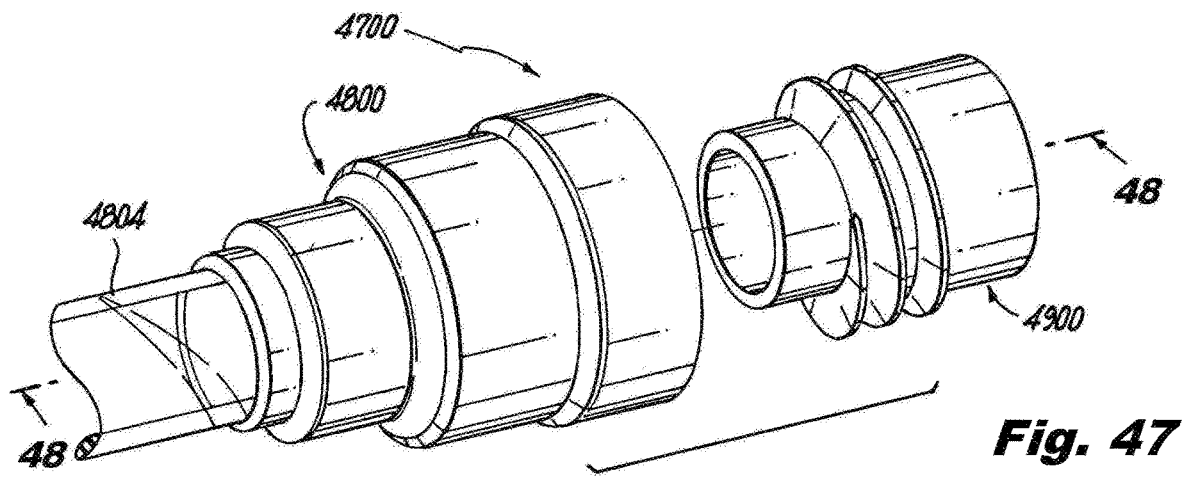
FIG. 47 is a perspective view of an alternate embodiment of a coupling assembly for use with a single lumen, showing a coupler and a mating device.
Figure 48:
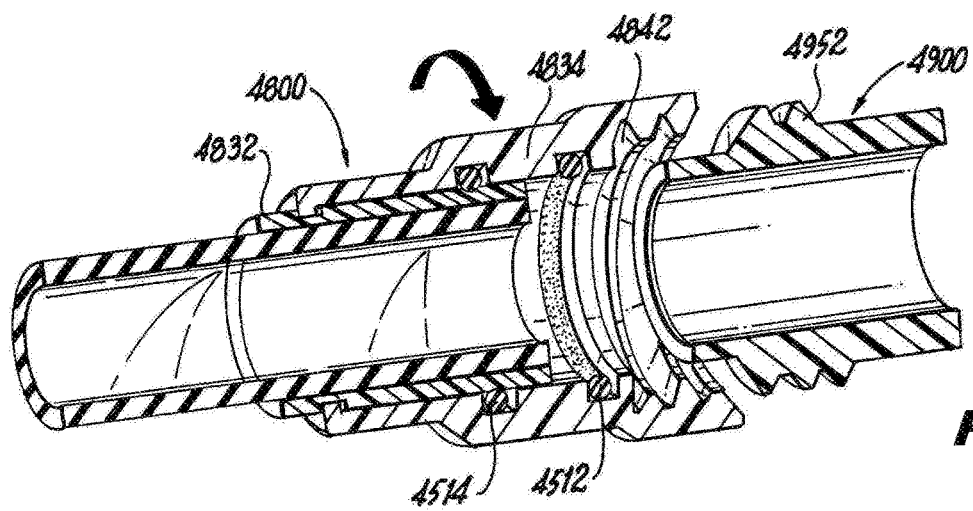
FIG. 48 is a cross-sectional view taken along line 48-48 of FIG. 47, showing rotating of the coupler to engage external threads of the mating device.
Figure 49:
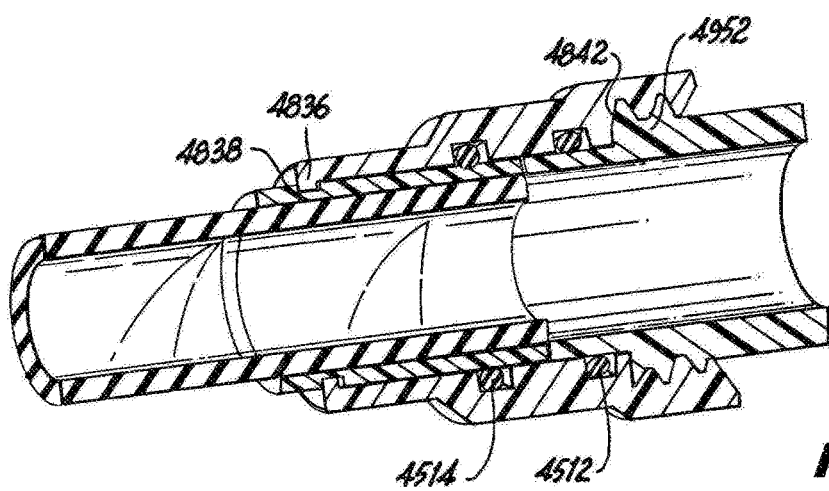
FIG. 49 is a cross-sectional view of the assembled coupler and the mating device of FIG. 47.

The coupling assembly 4700 shown in FIGS. 47-49 also includes a coupler 4800 with an inner sleeve 4832 and an outer sleeve 4834. The inner sleeve 4832 stays static to tubing 4804. The outer sleeve 4834 attaches to the inner sleeve 4832 with a tongue 4836 and annular groove feature 4838 (shown in FIG. 49) that positions the outer sleeve 4834 linearly to the inner sleeve 4832 but allows the outer sleeve 4834 free rotation. An O-ring 4514 is disposed between the inner and outer sleeves 4832, 4834 for sealing. Similar to outer sleeve 4534, outer sleeve 4834 has an internal thread and O-ring 4512 to engage and seal with an external thread 4952 of mating device 4900.

Figure 50:
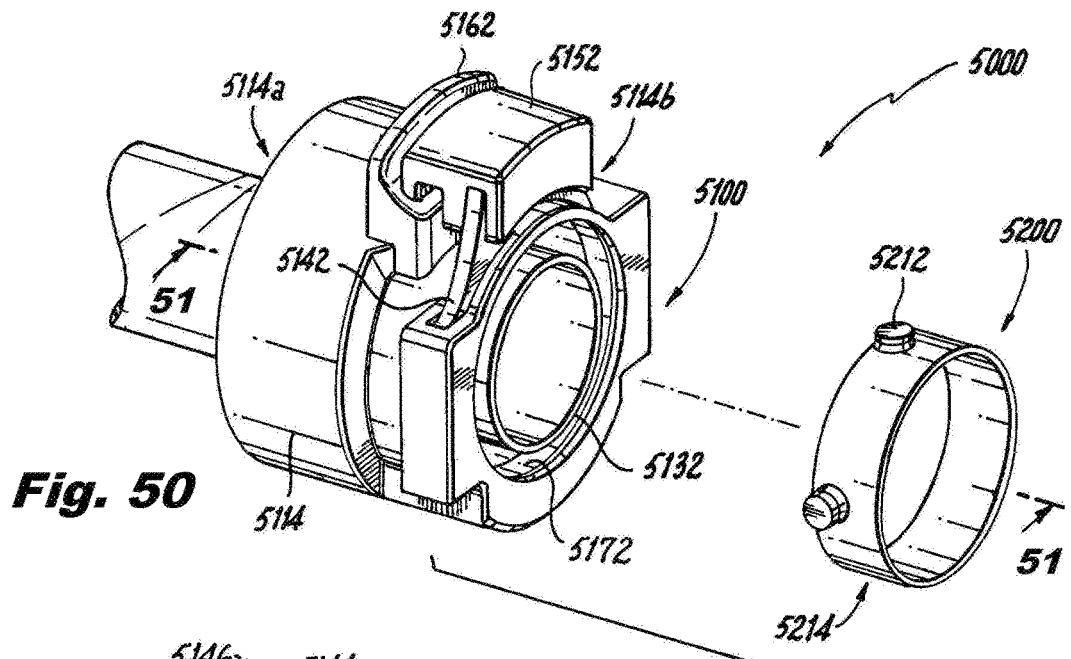
FIG. 50 is a perspective view of an alternate embodiment of a coupling assembly for use with a single lumen, showing a coupler and a mating device.
Figure 51:
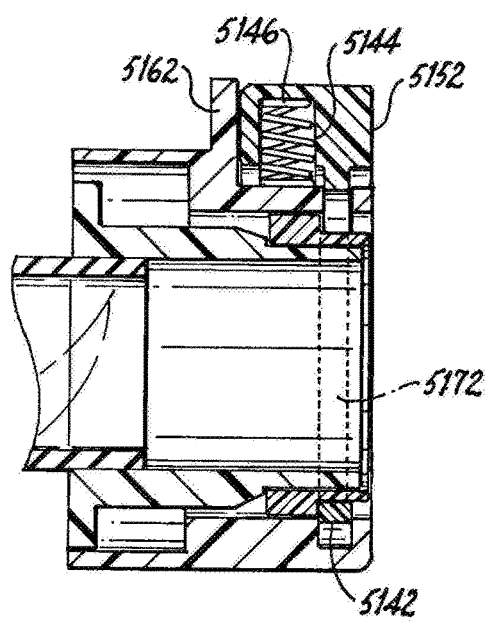
FIG. 51 is a cross-sectional view of the coupler taken along line 51-51 of FIG. 50, showing a spring loaded ring assembly to lock coupler with mating device.
Figure 52:
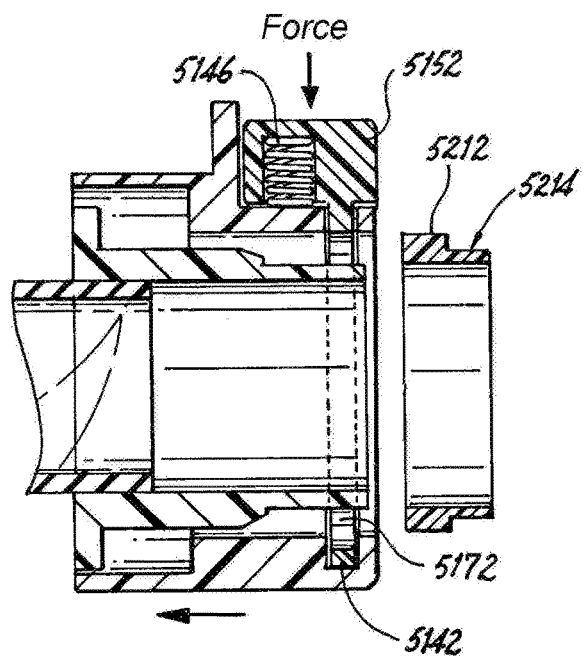
FIG. 52 is a cross-sectional view of the coupler of FIG. 50 showing removal of the coupler by pressing down on a tab of the ring assembly.
Figure 53:
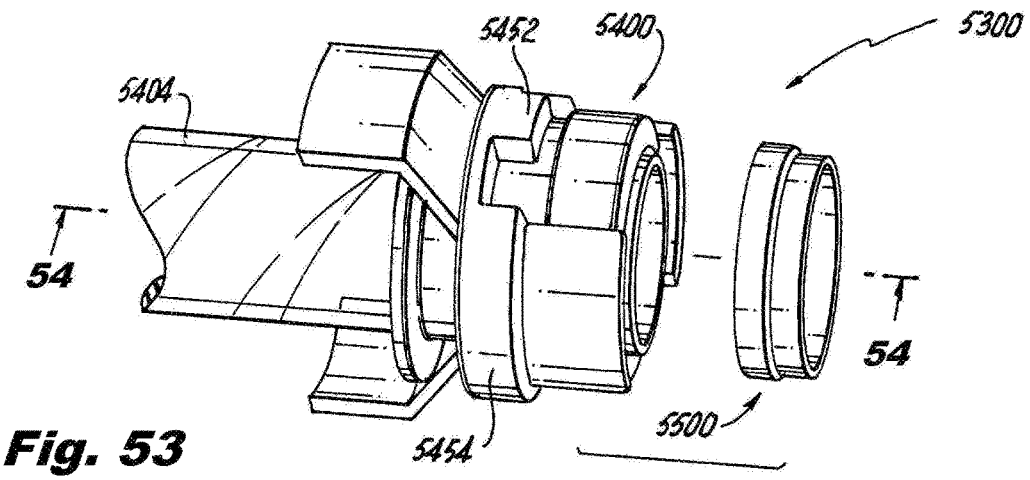
FIG. 53 is a perspective view of an alternate embodiment of a coupling assembly for use with a single lumen, showing a coupler and a mating device.
Figure 54:
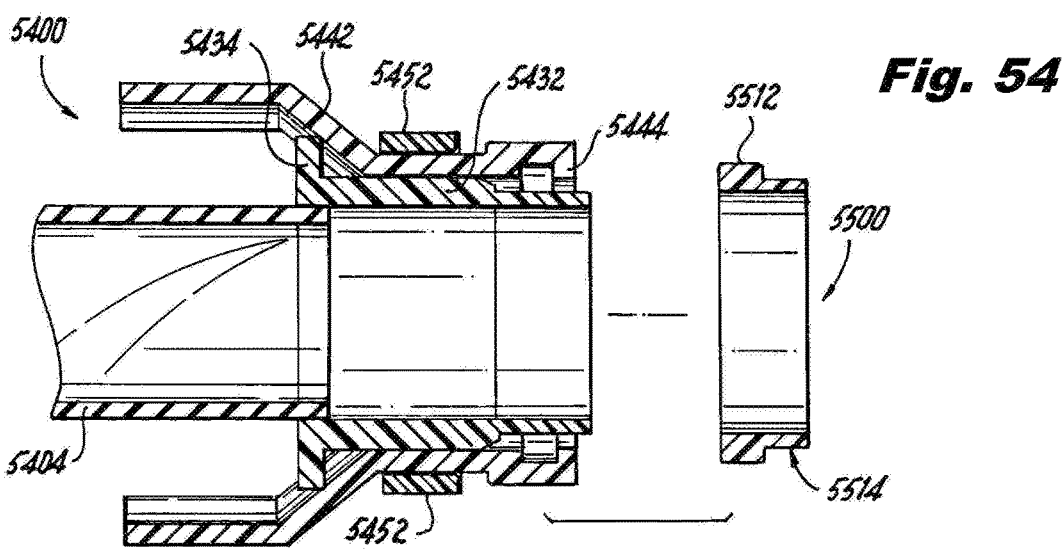
FIG. 54 is a cross-sectional view taken along line 54-54 of FIG. 53, showing pivoting latches of the coupler to engage an external ring of the mating device.
Figure 55:
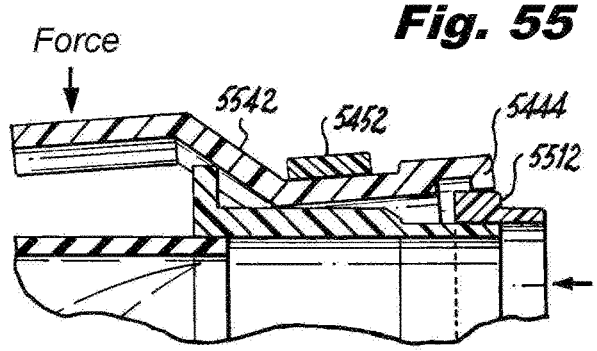
FIG. 55 is a cross-sectional view of the coupler, showing pivoting of the latch flexes a locking feature over post of mating device.
Figure 56:
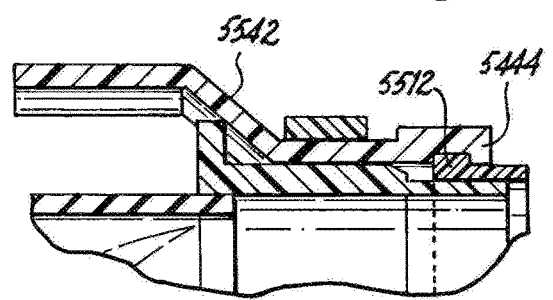
FIG. 56 is a cross-sectional view of the coupler, showing the latch fully locked with mating device.
Figure 57:
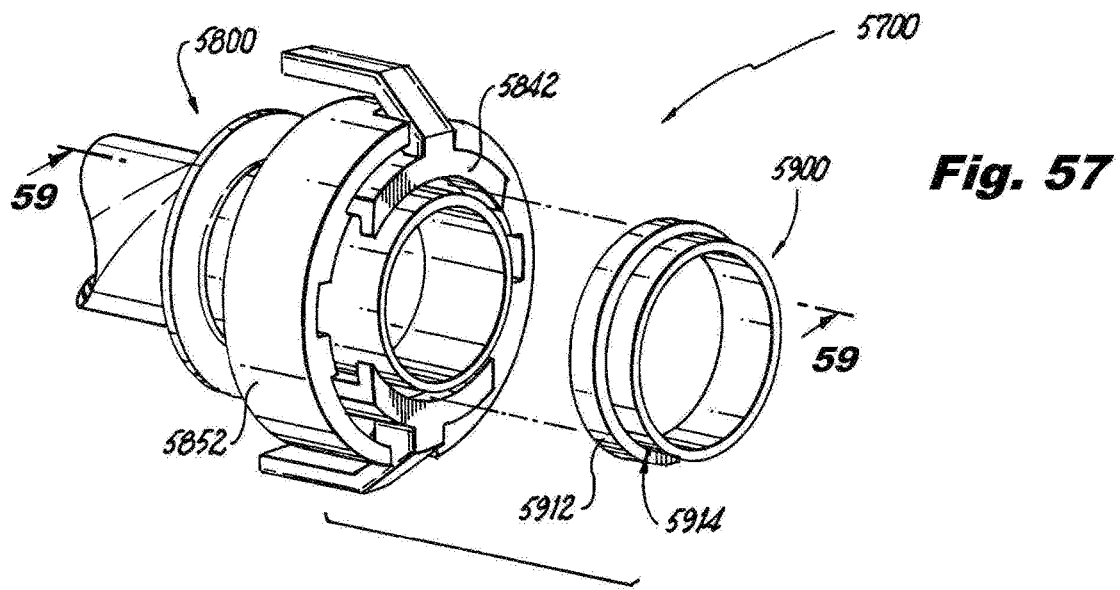
FIG. 57 is a perspective view of an alternate embodiment of a coupling assembly for use with a single lumen, showing a coupler and a mating device.
Figure 58:
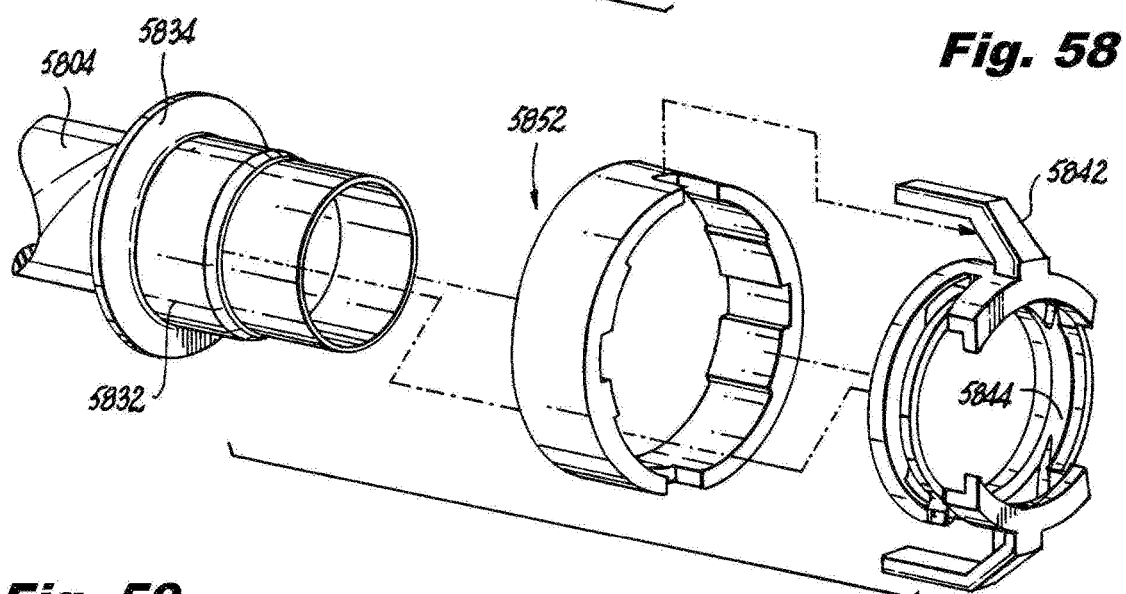
FIG. 58 is an exploded perspective view of the coupler and mating device of FIG. 57, showing pivoting latches of an outer sleeve of the coupler.
Figure 59:
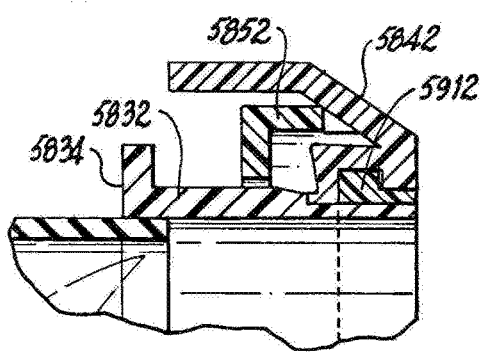
FIG. 59 is a cross-sectional view taken along line 59-59 of FIG. 57, showing the latches pivotable about a flange on the outer sleeve.
Figure 60:
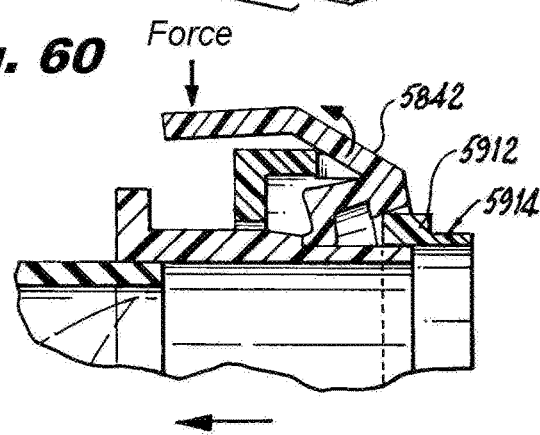
FIG. 60 is a cross-sectional view of the latch, showing pressure on the latch to pivot locking features of latches to engage posts of mating device.

With reference to FIGS. 50-52, another embodiment for a coupling assembly 5000 is shown. In this embodiment, a ring assembly is positioned at a distal portion 5114b of the coupler 5100. More specifically, the ring assembly includes a ring 5142 that is partially disposed within the coupler body 5114 surrounding the annular wall 5132. An external spring loaded tab 5152 extends proximally from the ring 5142 which allows for manipulating the ring 5142 to flex around posts 5212 of the mating device 5200 to engage therewith. As shown in FIG. 51, the tab 5152 includes a spring pocket 5144 to house a spring 5146 between the tab 5152 and coupler body 5114. The tab 5152 has a generally hook feature which mates with an opening 5162 of coupler body 5114.

To assemble, the coupler 5100 is pushed onto the mating device 5200 such that a cam face 5172 of the ring 5142 contacts posts 5212 of mating device 5200. Continued pressure will cause compression of the spring 5146 allowing the ring 5142 to flex over the posts 5212. When fully assembled, the cam face 5172 of the ring 5142 rests along external surface 5214 of mating device 5200. Pressure on the tab 5152 (shown in FIG. 52) flexes the ring 5142 and allows for the coupler 5100 to be pulled away from and off of mating device 5200. The embodiment shown in FIG. 50 illustrates round posts to secure the ring to the mating device, however other similar constructions such as an annular lip (e.g., as shown on mating device 5500 of FIG. 53), or the like, may be used.

FIGS. 53-56 show yet another alternate embodiment for a coupling assembly 5300 including a coupler 5400 having pivoting latches 5442. In this embodiment, an inner sleeve 5432 is integrally connected to tube 5404. Latches 5442 are positioned between the inner sleeve 5432 and an outer sleeve 5452. The inner sleeve 5432 includes flanges 5434 which act as a pivot point and prevent latches 5442 from moving linearly towards mating device 5500. The outer sleeve 5452 also has flexible tabs 5454 which hold the latches 5442 in a home position or a closed position.

The latches 5442 include a locking feature 5444 that engage an external ring (or lip) 5512 on the mating device 5500. To assemble, a user presses the latches 5442 and pivots them to flex locking feature 5444 away from the inner sleeve 5432 into an open position. Pressing the coupler 5400 towards the mating device 5500 allows the locking feature 5444 to push over the external ring 5512 (shown in FIG. 55). When the latches 5442 are released the flex tabs 5454 will rotate the latches 5442 back to a closed position and lock the latches 5442 such that the locking feature 5444 is positioned along surface 5514 of mating device (shown in FIG. 56).

To remove, the user presses the latches 5442 and releases the locking feature 5444 from the external ring 5512 and pulls the coupler 5400 away from the matching device 5500. An alternate embodiment of this design includes the latches opening while camming against the mating device when the coupler and mating device are pressed together so that the locking features self-lock without having to press on the latches.

FIGS. 57-60 illustrate another embodiment of a coupling assembly 5700 similar to coupling assembly 5300. In this embodiment, latches 5842 extend from a flexible ring 5844 that snaps into outer sleeve 5852 and pivots against outer sleeve 5852. When assembled, outer sleeve 5852 fits over inner sleeve 5832 with inner sleeve 5832 including flanges 5834 to prevent movement of outer sleeve 5852. Pressing and releasing latches 5842 allows ring 5844 to flex outwardly to push over posts 5912 (shown in FIG. 60) or release to pull coupler away from mating device 5900. This design can be used either by pivoting the latches (as shown) or by the latches camming open automatically during engagement with posts of the matching device.

Figure 61:
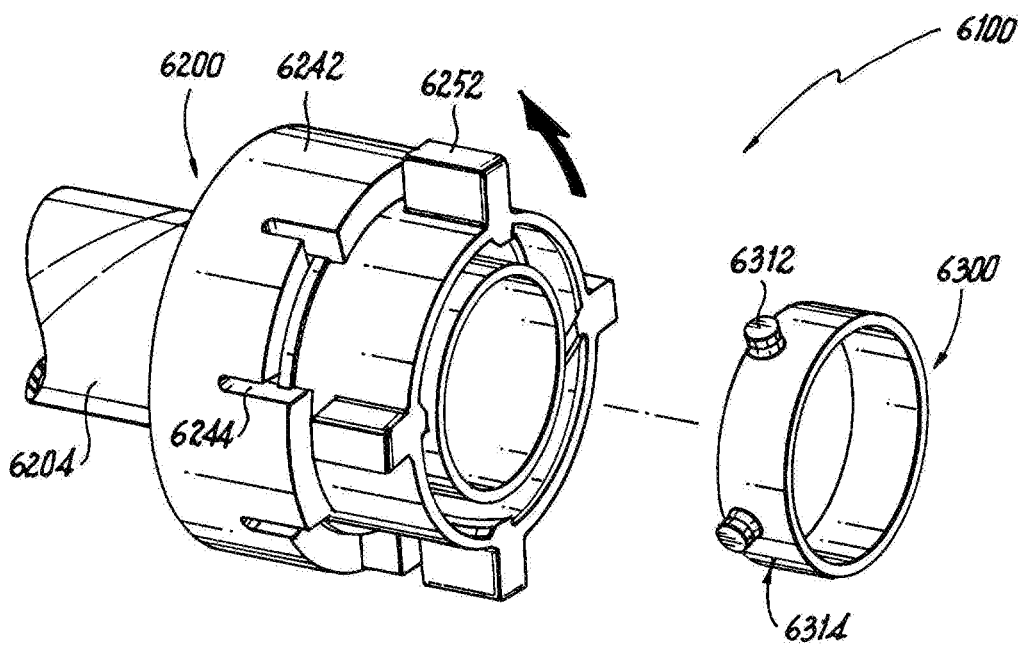
FIG. 61 is a perspective view of an alternate embodiment of a coupling assembly for use with a single lumen, showing a coupler and a mating device.
Figure 62:
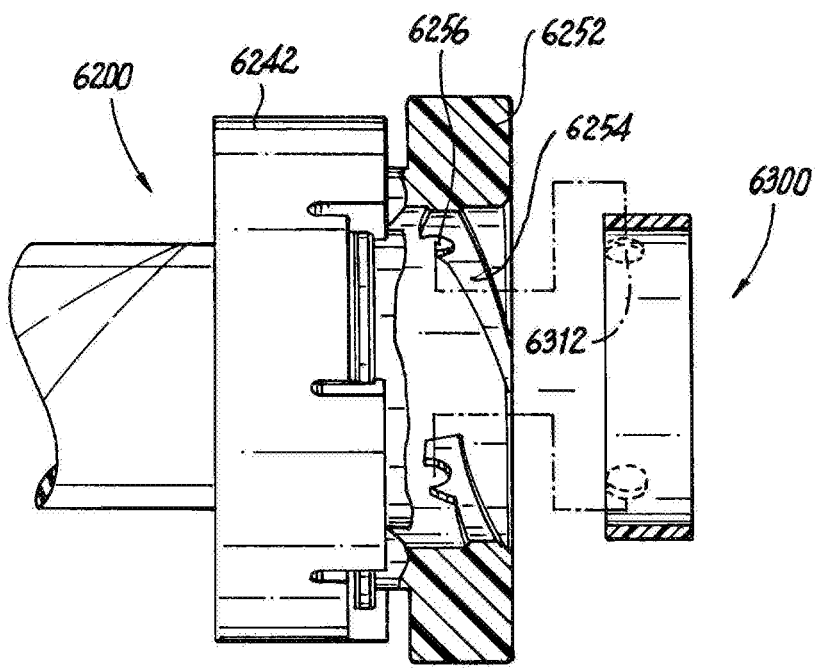
FIG. 62 is an exploded view of the coupler and mating device of FIG. 61, showing posts of mating device locking into threads of coupler to assemble coupler and mating device.

FIGS. 61-62 illustrate an alternate embodiment of a coupling assembly 6100 having a static ring 6242 and a rotating ring 6252. The static ring 6242 connects to tubing 6204 and the rotating ring 6252 has an internal thread 6254 (shown in FIG. 62) to engage mating device 6300. The thread 6254 includes locking features 6256 that lock the rotating ring 6252 to posts 6312 of the mating device 6300 when fully assembled. To engage the coupler 6200 to mating device 6300, a user rotates the rotating ring 6252 onto the mating device posts 6312. The posts 6312 engage the locking features 6256 and secure the coupler 6200 thereto. To remove, the user simply reverse rotates the rotating ring 6252 to release the posts 6312 from the locking features 6256 and pulls coupler 6200 away from mating device 6300.

Figure 63:
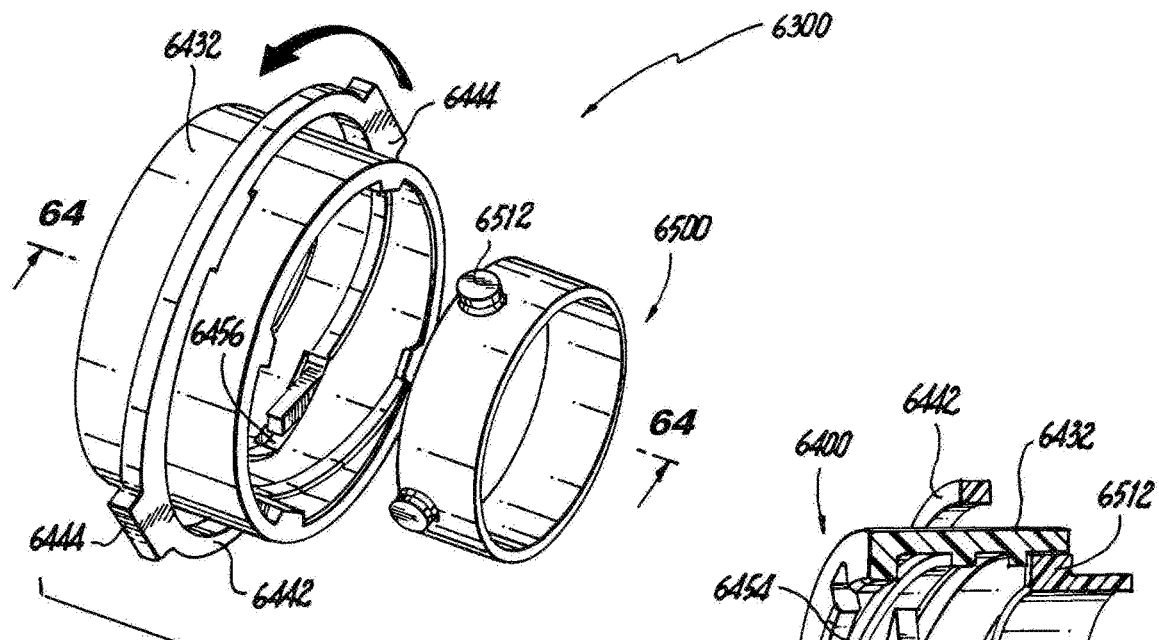
FIG. 63 is a perspective view of an alternate embodiment of a coupling assembly for use with a single lumen, showing a coupler and a mating device.
Figure 64:
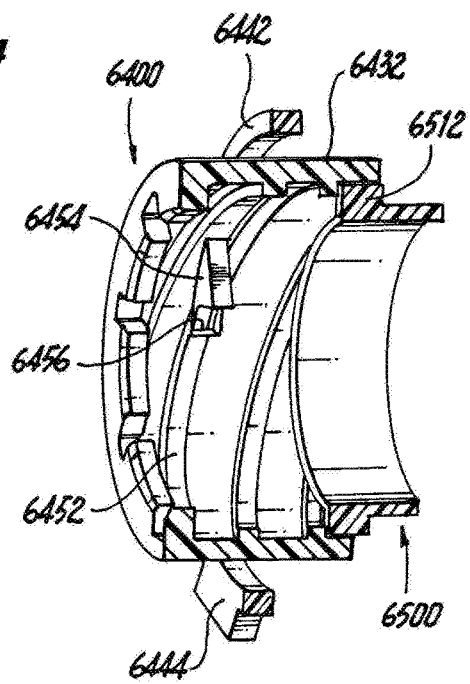
FIG. 64 is a cross-sectional view of the coupler taken along line 64-64 of FIG. 63 showing finger tabs on a locking ring that extend into threads of the coupler.
Figure 65:
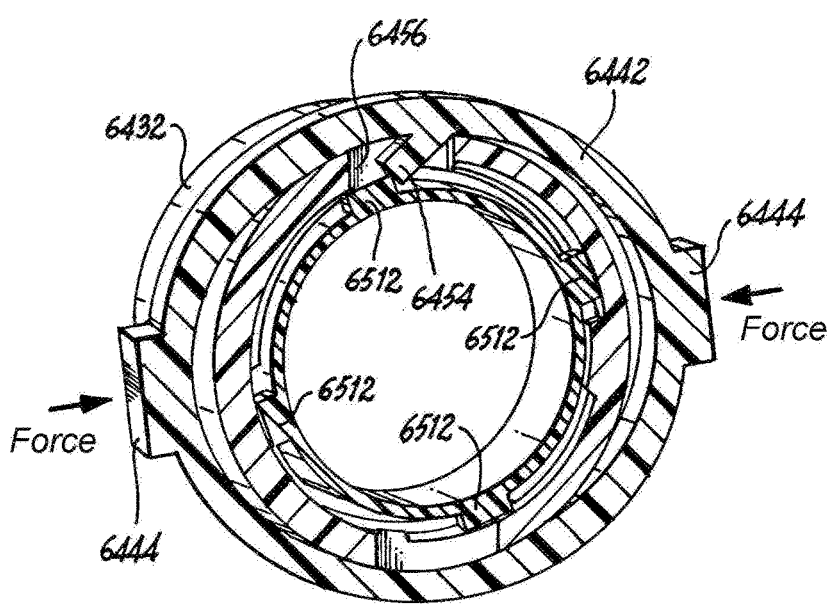
FIG. 65 is a perspective view of the coupler of FIG. 63, showing pressure on finger tabs disengages coupler from mating device.

Referring to FIGS. 63-65, an alternate embodiment for a coupler is shown. This design is includes an outer sleeve 6432 positioned over coupler body (not shown for clarity) with a locking ring 6442. As shown in FIG. 64, the locking ring 6442 has flexible tabs 6454 that extend through slots 6456 of an internal thread 6452 within outer sleeve 6432. As the coupler is screwed onto mating device 6500, the flex tabs 6454 contact posts 6512 of the mating device 6500 and flex over the posts 6512 with continued pressure to lock coupler in place. To remove, a user squeezes finger tabs 6444 on locking ring 6442 which will lift the flexible tabs 6454 off posts 6512 and allow for unscrewing the coupler away from the mating device 6500.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. A coupling system for connecting a dual lumen tube set to a trocar comprising:
   a) a trocar connector having two coaxial flow passages formed therein including an inner flow passage defined by an inner annular wall and an outer flow passage defined between the inner annular wall and an outer annular wall, wherein a plurality of circumferentially spaced apart posts project radially outwardly from the outer annular wall of the trocar connector;
   b) a dual lumen tube set including a first tube having a first diameter and a second tube having a second diameter that is greater than the first diameter;
   c) a coupling including a generally cylindrical body having a first end portion configured to mate with the two coaxial flow passages of the trocar connector and a second end portion configured for attachment to the first tube and the second tube of the dual lumen tube set, the first end portion of the body having an inner flow passage defined by an inner annular wall for establishing fluid communication with the inner flow passage of the trocar connector and an outer flow passage defined between the inner annular wall of the body and an outer annular wall of the body for establishing fluid communication with the outer flow passage of the trocar connector, the second end portion of the body including first and second parallel interior recesses, wherein a central axis of the first interior recess is spaced apart from and parallel to a central axis of the second interior recess, and wherein the first interior recess is dimensioned and configured to receive a distal end portion of the first tube of the dual lumen tube set and the second interior recess is dimensioned and configured to receive a distal end portion of the second tube of the dual lumen tube set; and
   d) a shroud rotatably supported on the body of the coupling and including an internal ring having an inner annular surface with an internal thread for rotationally engaging the plurality of circumferentially spaced apart posts that project radially outwardly from the outer annular wall of the trocar connector upon axial rotation of the shroud relative to the body of the coupling, wherein the internal ring includes a plurality of circumferentially spaced apart radially inwardly extending arcuate tabs configured to snap fit into corresponding arcuate slots formed in an outer surface of the coupling to restrict rotational movement therebetween, wherein the internal ring further includes a plurality of axially extending circumferentially spaced apart flexible fingers which engage with a plurality of circumferentially spaced apart ramps in the shroud that ratchet together when torque is applied to the flexible fingers, and wherein the plurality of arcuate tabs are located between the internal thread and the plurality of flexible fingers.

2. The coupling system as recited in claim 1, wherein the inner annular wall of the coupling is dimensioned and configured to fit within the inner annular wall of the trocar connector and the outer annular wall of the coupling is dimensioned and configured to fit within the outer annular wall of the trocar connector.

3. The coupling system as recited in claim 1, wherein the first interior recess is configured for receiving the first tube of the dual lumen tube set to communicate with the outer flow passage of the coupling, and the second interior recess is configured for receiving the second tube of the dual lumen tube set to communicate with the inner flow passage of the coupling.

4. The coupling system as recited in claim 1, wherein the first and second interior recesses are both off set from a central axis of the body of the coupling.

5. The coupling system as recited in claim 1, wherein the shroud and the internal ring are integrally combined into a single shroud assembly.

6. A coupling system for connecting a dual lumen tube set to a trocar comprising:
   a) a trocar connector having two coaxial flow passages formed therein, wherein a plurality of circumferentially spaced apart posts project radially outwardly from an outer annular wall of the trocar connector;
   b) a dual lumen tube set including a first tube having a first diameter and a second tube having a second diameter that is greater than the first diameter;
   c) a coupling including a generally cylindrical body having a first end portion configured to mate with the two coaxial flow passages of the trocar connector and a second end portion configured for attachment to the first tube and the second tube of the dual lumen tube set, the second end portion of the body including first and second parallel interior recesses off set from a central axis of the body, wherein a central axis of the first interior recess is spaced apart from and parallel to a central axis of the second interior recess, and wherein the first interior recess is dimensioned and configured to receive a distal end portion of the first tube of the dual lumen tube set and the second interior recess is dimensioned and configured to receive a distal end portion of the second tube of the dual lumen tube set; and d) a shroud rotatably supported on the body of the coupling and including an internal ring having an inner annular surface with an internal thread for rotationally engaging the plurality of circumferentially spaced apart posts that project radially outwardly from the outer annular wall of the trocar connector upon axial rotation of the shroud relative to the body of the coupling, wherein the internal ring includes a plurality of circumferentially spaced apart radially inwardly extending arcuate tabs configured to snap fit into corresponding arcuate slots formed in an outer surface of the coupling to restrict rotational movement therebetween, and wherein the internal ring further includes a plurality of axially extending circumferentially spaced apart flexible fingers which engage with a plurality of circumferentially spaced apart ramps in the shroud that ratchet together when adequate torque is applied to the flexible fingers, and wherein the plurality of arcuate tabs are located between the internal thread and the plurality of flexible fingers.

7. The coupling system as recited in claim 6, wherein the trocar connector has an inner flow passage defined by an inner annular wall and an outer flow passage defined between the inner annular wall and the outer annular wall.

8. The coupling system as recited in claim 7, wherein the first end portion of the body of the coupling has an inner flow passage defined by an inner annular wall for establishing fluid communication with the inner flow passage of the trocar connector and an outer flow passage defined between the inner annular wall of the body of the coupling and an outer annular wall of the body of the coupling for establishing fluid communication with the outer flow passage of the trocar connector.

9. The coupling system as recited in claim 8, wherein the inner annular wall of the body of the coupling is dimensioned and configured to fit within the inner annular wall of the trocar connector and the outer annular wall of the body of the coupling is dimensioned and configured to fit within the outer annular wall of the trocar connector.

10. The coupling system as recited in claim 9, wherein the first interior recess is configured for receiving the first tube of the dual lumen tube set to communicate with the outer flow passage of the body of the coupling, and the second interior recess is configured for receiving the second tube of the dual lumen tube set to communicate with the inner flow passage of the body of the coupling.

11. The coupling system as recited in claim 6, wherein the shroud and the internal ring are integrally combined into a single shroud assembly.

12. A coupling for connecting a dual lumen tube set to a trocar comprising:

a generally cylindrical body having a first end portion configured to mate with a trocar connector having two co-axial flow passages and a second end portion configured for attachment to a dual lumen tube set, the first end portion of the body having an inner flow passage defined by an inner annular wall for establishing fluid communication with an inner flow passage of the trocar connector and an outer flow passage defined between the inner annular wall of the body and an outer annular wall of the body for establishing fluid communication with an outer flow passage of the trocar connector, the second end portion of the body including first and second parallel interior recesses, wherein a central axis of the first interior recess is spaced apart from and parallel to a central axis of the second interior recess, and wherein the first interior recess is dimensioned and configured to receive a distal end portion of a first tube of the dual lumen tube set and the second interior recess is dimensioned and configured to receive a distal end portion of a second tube of the dual lumen tube set, and wherein a shroud is rotatably supported on the body and includes an internal ring having an inner annular surface with an internal thread for rotationally engaging the trocar connector upon axial rotation of the shroud relative to the body, wherein the internal ring includes a plurality of circumferentially spaced apart radially inwardly extending arcuate tabs configured to snap fit into corresponding arcuate slots formed in an outer surface of the coupling to restrict rotational movement therebetween, and wherein the internal ring further includes a plurality of axially extending circumferentially spaced apart flexible fingers which engage with a plurality of circumferentially spaced apart ramps in the shroud that ratchet together when adequate torque is applied to the flexible fingers, and wherein the plurality of arcuate tabs are located between the internal thread and the plurality of flexible fingers.

13. A coupling as recited in claim 12, wherein the first interior recess has a first inner diameter and the second interior recess has a second inner diameter that is greater than the first inner diameter of the first interior recess.

14. A coupling as recited in claim 12, wherein the shroud and the internal ring are integrally combined into a single shroud assembly.

* * * * *